(12) United States Patent
Yoon et al.

(10) Patent No.: US 12,048,853 B2
(45) Date of Patent: Jul. 30, 2024

(54) LIGHT IRRADIATION APPARATUS

(71) Applicant: SEOUL VIOSYS CO., LTD., Gyeonggi-do (KR)

(72) Inventors: Yeong Min Yoon, Gyeonggi-do (KR); A Young Lee, Gyeonggi-do (KR); Hee Ho Bae, Gyeonggi-do (KR); Joon-Pio Hong, Seoul (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 931 days.

(21) Appl. No.: 16/539,620

(22) Filed: Aug. 13, 2019

(65) Prior Publication Data
US 2020/0054893 A1 Feb. 20, 2020

Related U.S. Application Data

(60) Provisional application No. 62/825,993, filed on Mar. 29, 2019, provisional application No. 62/718,646, filed on Aug. 14, 2018.

(51) Int. Cl.
*A61N 5/06* (2006.01)
*A61M 13/00* (2006.01)

(52) U.S. Cl.
CPC .......... *A61N 5/0624* (2013.01); *A61M 13/003* (2013.01); *A61N 5/062* (2013.01);
(Continued)

(58) Field of Classification Search
CPC ................. A61N 5/0624; A61N 5/062; A61N 2005/0629; A61N 2005/0661;
(Continued)

(56) References Cited

U.S. PATENT DOCUMENTS

2003/0047742 A1 * 3/2003 Hen .................... H01L 25/0756
257/89
2003/0153962 A1   8/2003 Cumbie
(Continued)

FOREIGN PATENT DOCUMENTS

KR   10-2005-0096139 A   10/2005
KR   10-2015-0032994 A    4/2015
(Continued)

OTHER PUBLICATIONS

International Search Report for Application No. PCT/KR2019/010365 dated Oct. 29, 2019, 3 pages.
(Continued)

*Primary Examiner* — Joseph M Dietrich
*Assistant Examiner* — Michael T. Holtzclaw
(74) *Attorney, Agent, or Firm* — Perkins Coie LLP

(57) ABSTRACT

A light irradiation apparatus includes first and second light sources that emit first light and second light, respectively. The first and the second lights have mutually different wavelengths at timings close to each other, regardless of overlap between the first light and the second light. The first light has a wavelength band for inducing destruction of bacteria by damaging a cell of the bacteria as the first light acts on a photosensitizer present in the bacteria. The second light has a wavelength band for inducing the destruction of the bacteria by changing the structure of a genetic material present in the cell of the bacteria. A dose of the second light source is less than 1/10 of a dose of the first light source.

19 Claims, 21 Drawing Sheets

(52) U.S. Cl.
CPC ............... *A61M 2202/0208* (2013.01); *A61N 2005/0629* (2013.01); *A61N 2005/0661* (2013.01); *A61N 2005/0663* (2013.01)

(58) Field of Classification Search
CPC ............ A61N 2005/0663; A61N 5/06; A61M 13/003; A61M 2202/0208; A61L 2/10; A61L 2202/14
See application file for complete search history.

(56) References Cited

U.S. PATENT DOCUMENTS

| | | | |
|---|---|---|---|
| 2006/0049415 A1* | 3/2006 | Liao | H01L 33/08 257/97 |
| 2006/0167531 A1 | 7/2006 | Gertner et al. | |
| 2007/0208395 A1* | 9/2007 | Leclerc | A61N 5/0616 607/86 |
| 2008/0071330 A1* | 3/2008 | Quisenberry | A61M 35/30 607/88 |
| 2008/0103560 A1* | 5/2008 | Powell | A61N 5/0616 607/94 |
| 2015/0179879 A1* | 6/2015 | Yang | H05B 33/06 257/98 |
| 2017/0304472 A1* | 10/2017 | Neister | A61L 9/20 |
| 2018/0056087 A1* | 3/2018 | Ribeiro | A61L 15/00 |
| 2018/0093107 A1 | 4/2018 | Ball | |
| 2018/0318599 A1* | 11/2018 | Van Bommel | H05B 47/155 |
| 2019/0099613 A1* | 4/2019 | Estes | A61N 5/0616 |

FOREIGN PATENT DOCUMENTS

| | | |
|---|---|---|
| KR | 10-2015-0143456 A | 12/2015 |
| KR | 10-1592145 B1 | 2/2016 |
| KR | 20160070930 A | 6/2016 |
| WO | 2006081312 A2 | 8/2006 |
| WO | 2009004412 A1 | 1/2009 |

OTHER PUBLICATIONS

Extended Search Report issued in corresponding EP Application No. 19850416.9, issued Apr. 8, 2022, 6 pages.

English translation of Indian Examination Report from corresponding Indian Application No. 202137010578 dated Sep. 16, 2022.

English translation of office action from corresponding Chinese Patent Application No. 201980003183.3 dated Sep. 5, 2023, (16 pages).

* cited by examiner

LIGHT IRRADIATION APPARATUS

CROSS-REFERENCE TO RELATED APPLICATIONS

This application claims the benefit of U.S. Provisional Applications No. 62/718,646, filed on Aug. 14, 2018, and No. 62/825,993, filed on Mar. 29, 2019, which are hereby incorporated by reference for all purposes as if fully set forth herein.

BACKGROUND

Embodiments of the inventive concept described herein relate to light irradiation apparatuses.

Recently, various medical devices using ultraviolet (UV) light have been developed. In general, it is well known that the UV light has a sterilization effect. A conventional UV curing device employs a traditional UV lamp, operates the UV lamp near a skin, and irradiates the UV light to a part to be cured.

However, the UV light causes an adverse effect such as skin aging or cancer, in addition to the sterilization effect. Accordingly, there is a need to obtain the sterilization effect in a way that avoid any harmful influence exerted on a human body.

SUMMARY

Embodiments of the inventive concept provide a light irradiation apparatus capable of obtaining a higher sterilization effect while minimizing an adverse effect on a human body.

According to an exemplary embodiment of the inventive concept, a light irradiation apparatus includes first and second light sources to emit first light and second light having mutually different wavelengths, respectively, at timings close to each other regardless of overlap between the first light and the second light, the first light has a wavelength band for inducing destruction of bacteria by damaging a cell as the first light acts on a photosensitizer present in the bacteria, the second light has a wavelength band for inducing the destruction of the bacteria by changing the structure of a genetic material present in the cell of the bacteria, and a dose of the second light source is less than 1/10 of a dose of the first light source.

According to an exemplary embodiment of the inventive concept, the first light may be blue light, the second light may be ultraviolet light, and the second light may be irradiated with a daily maximum irradiation amount of about 3 mJ/cm$^2$.

According to an exemplary embodiment of the inventive concept, the first wavelength may be in the range of about 400 nm to about 420 nm or the range of about 455 nm to about 470 nm.

According to an exemplary embodiment of the inventive concept, the second wavelength may have a wavelength of ultraviolet C (UVC), and the second wavelength may be in the range of about 210 nm to about 280 nm, and may be, in more detail, in the range of about 220 nm to about 230 nm.

According to an exemplary embodiment of the inventive concept, the first light and the second light may be simultaneously emitted.

According to an exemplary embodiment of the inventive concept, the first light and the second light may be emitted for mutually different times, and a duration, in which one of the first light and the second light is emitted, is at least partially overlapped with a duration in which a remaining light is emitted.

According to an exemplary embodiment of the inventive concept, one of the first light and the second light may be continuously emitted, and a remaining one of the first light and the second light may be emitted while being turned on or off.

According to an exemplary embodiment of the inventive concept, a duration, in which one of the first light and the second light is emitted, is not overlapped with a duration in which a remaining light of the first light and the second light is emitted.

According to an exemplary embodiment of the inventive concept, a starting point of a duration in which the first light is emitted is different from a starting point of a duration in which the second light is emitted.

According to an exemplary embodiment of the inventive concept, an irradiation area of the first light source may be overlapped with an irradiation area of the second light source.

According to an exemplary embodiment of the inventive concept, the light irradiation apparatus may further include a controller to control the first light source and the second light source, and the controller may control at least one of an intensity and an irradiation time of each of the first light and the second light.

According to an exemplary embodiment of the inventive concept, the light irradiation apparatus may further include a third light source connected with the controller to emit light having a visible light wavelength.

According to an exemplary embodiment of the inventive concept, the light irradiation apparatus may further include an oxygenator connected with the controller to supply oxygen.

According to an exemplary embodiment of the inventive concept, he light irradiation apparatus may further include an input unit connected with the controller to input data on a user or an external environment, and the controller may control the first and second light sources based on the data from the input unit.

According to an exemplary embodiment of the inventive concept, on an assumption that a harmless dose per day is an allowable dose when the second light is applied to a human body, the second light source emits the second light within the allowable dose.

The light radiation device may be used to cure a human body, and may be, for example, used to cure an acute wound.

As described above, embodiments of the inventive concept provide a light irradiation apparatus having higher sterilization power while being harmless to a human body.

BRIEF DESCRIPTION OF DRAWINGS

The above and other objects and features of the inventive concept will become apparent by describing in detail exemplary embodiments thereof with reference to the accompanying drawings.

FIGS. 18A and 18B are photographs obtained by capturing images of the shape of the wound area based on days, in which FIG. 15A is a photograph of wounds in a non-irradiation group, and FIG. 15B is a photograph of wounds in the light irradiation group;

DETAILED DESCRIPTION OF EMBODIMENTS

Figure 1A:
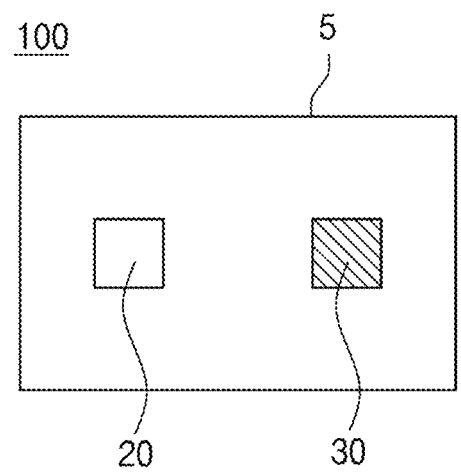
FIG. 1A is a plan view illustrating a light irradiation apparatus, according to one or more embodiments of the present disclosure.

While the inventive concept is susceptible to various modifications and alternative forms, specific embodiments thereof are shown by way of examples in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the invention.

Hereinafter, exemplary embodiments of the inventive concept will be described in more detail with reference to accompanying drawings.

The inventive concept relates to a light irradiation apparatus capable of sterilizing a target to be sterilized by applying sterilizing light to the target. In this case, the target to be sterilized is a microorganism such as a bacterium, a germ, or mold existing on a part of various articles, various animals, or a human body, or the surface (or skin) thereof. Since the target, such as a bacterium, a germ, or mold, to be sterilized exists on at least a part of various articles, a human body, or an animal, for example, a skin, the human body or the animal is referred to as the target to be sterilized below.

In particular, according to one or more embodiments of the present disclosure, the light irradiation apparatus may be used to cure a wound. When a target to be sterilized is a human body and the skin of the human body is wounded, it is necessary to sterilize a pathogen at the wounded part, and a sterilizing device according to one embodiment of the inventive concept may be used to sterilize the pathogen in the wound. In this case, the pathogens refer to microorganisms such as bacteria, viruses, germs, fungi, protists, or molds. According to one or more embodiments of the present disclosure, the light irradiation apparatus may be used for various wounds such as a wound, an ulcer, surgical site infection, a laceration, an incised wound, or a punctured wound.

Figure 1B:
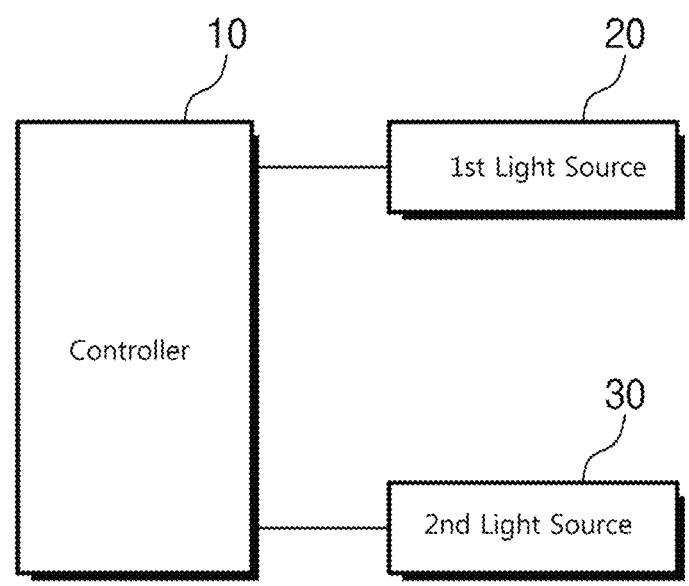
FIG. 1B is a block diagram illustrating a light irradiation apparatus, according to one or more embodiments of the present disclosure.

FIG. 1A is a plan view illustrating a light irradiation apparatus, according to one or more embodiments of the present disclosure, and FIG. 1B is a block diagram illustrating the light irradiation device according to one or more embodiments of the present disclosure;

Referring to FIGS. 1A and 1B, according to one or more embodiments of the present disclosure, a light irradiation apparatus 100 includes a first light source 20 to emit first light, a second light source 30 to emit second light, and a substrate 5 to mount the first and second light sources 20 and 30 thereon.

Since the first light source 20 and the second light source 30 are mounted on the substrate 5, the substrate 5 is not limited to a specific form and may be provided in various forms sufficient to mount the first and second light sources 20 and 30 thereon. The substrate 5 may be provided in the form of including a wiring to supply power to the first and second light sources 20 and 30. The substrate 5 may include, for example, a metallic substrate or a printed circuit board including the wiring.

The first and second light sources 20 and 30 emit light having mutually different wavelength bands.

The first light source 20 emits first light of a first wavelength. The first wavelength corresponds to visible light, and is a wavelength corresponding to blue light of the visible light. The first light may correspond to light in a wavelength band of about 400 nm to about 500 nm. In some embodiments, the first wavelength may be in the range of about 400 nm to about 500 nm, about 400 nm to about 420 nm, or about 455 nm to about 470 nm. Alternatively, in other embodiments, the first wavelength may be in the range of about 400 nm to about 410 nm, for example, may be 405 nm.

The second light source 30 emits the second light in the UV wavelength band. In other words, the second light may be light having a wavelength band in the range of about 100 nm to about 400 nm, and may be UVA, UVB, or UVC. The UVA may have a wavelength band in the range of about 315 nm to about 400 nm, the UVB may have a wavelength band in the range of about 280 nm to about 315 nm, and the UVC may have a wavelength band in the range of about 100 nm to about 280 nm. In some embodiments, the second light may correspond to the UVC, and may have a wavelength band in the range of about 240 nm to about 280 nm. In other embodiments, more specifically, the second light may be light having the wavelength of 275 nm. Alternatively, in one embodiment of the inventive concept, the second wavelength may be in the range of about 220 nm to about 230 nm, for example, may be 225 nm.

When the second light is applied to bacteria, DNAs in the bacteria absorbs the second light, and the DNA structure is changed by the energy of the second light. The absorption of light by the DNA causes the binding of thymine and adenine in the DNA to be broken. This is because a base such as purine or pyrimidine, which constitutes the DNA, strongly absorbs UV light. As a result of light absorption, a thymine dimer is formed. This process leads to the DNA mutation, and the mutated DNA causes the death of the bacteria since the mutated DNA has no ability of cell proliferation. The DNA may absorb light having a wavelength band in the range of about 240 nm to about 280 nm.

In some embodiments, the first light source 20 may include at least one light emitting diode that emits the first light, and the second light source 30 may include at least one light emitting diode that emits the second light. The structure of the light emitting diodes to emit the first light and the second light will be described later.

An irradiation area irradiated with light emitted from the first light source 20 may at least partially overlap with an irradiation area irradiated with light emitted from the second light source 30. In some embodiments, the irradiation area irradiated with light emitted from the first light source 20 may be substantially identical to the irradiation area irradiated with light emitted from the second light source 30.

The first light acts on a photosensitizer, which is present inside the microorganism, such as a bacterium, a germ, or mold, to damage a cell thereof, thereby inducing the eradication of the microorganism.

For example, when the microorganism is irradiated with the first light, the photosensitizer present inside the microorganism absorbs the first light, such that cytotoxic reactive oxygen species having cytotoxicity increase inside the microorganism. The cytotoxic reactive oxygen species, which are chemically reactive molecules, including oxygen atoms, represent high reactivity due to unpaired electrons in the molecule. The cytotoxic reactive oxygen species, which abnormally rapidly increase in the cell, damage the cell structure, thereby inducing the death of the cell.

The first light exhibits higher sterilization power particularly in the range of 400 nm to 420 nm and the range of 455 nm to 470 nm, which is owing to porphyrin, which is a photosensitizer present in the microorganism (for example, bacteria). Porphyrin is a pigment that is essential for the process of transferring oxygen inside a cell. Porphyrin represents higher absorbance in the range of about 402 nm to about 420 nm, and may absorb the wavelength in the range of about 455 nm to about 470 nm. In one or more embodiments of the present disclosure, porphyrin may be used for the purpose of destroying specific bacteria by controlling the wavelength and intensity of the first light because the content of the porphyrin is varied depending on the type of bacteria. When the first light is applied to bacteria, the porphyrin in the bacteria absorbs the first light, and reactive oxygen species are produced in the cell of the bacteria due to the energy of the first light. The reactive oxygen species are accumulated in cells of the bacteria to oxidize cell walls of the bacteria, thereby destroying the bacteria.

The second light is classified into UVC (in the range of 200 nm to 280 nm), UVB (in the range of 280 nm to 320 nm), and UVA (in the range of 320 nm to 400 nm) depending on wavelengths and causes the damage to deoxyribonucleic acid (DNA) which is a genetic material. The second light may be used to sterilize the microorganism such as a bacterium. DNA, which is a genetic material present in a cell, has genetic data that are expressed in proteins. A cell survives through proteins expressed from DNA, and divides (multiply) through the DNA replication process. When the DNA of the cell is damaged, the protein may not be normally produced, and the DNA may not be replicated, so the cell may be destroyed instead of growing.

When UV is irradiated to DNA, a pyrimidine dimer, which is a bond between adjacent pyrimidine bases in the DNA, is formed. The pyrimidine dimers include cyclobutane pyrimidine dimers and pyrimidine-pyrimidone 6-4 photoproducts. In a part of the DNA, which the pyrimidine dimers are produced, a gene sequence is not sufficiently recognized, so the expression of a protein is inhibited, and the DNA is not sufficiently replicated. Accordingly, the DNA is prevented from being proliferated, and is destroyed. Even ribonucleic acid (RNA) is destroyed through the same mechanism.

Particularly, the UVC of the UV wavelength band is a representative wavelength used for sterilization and mainly applied to a sterilizer.

In one or more embodiments of the present disclosure, the first light source 20 and the second light source 30 are connected with a controller 10 to drive and control the first light source 20 and the second light source 30 and a power supply unit 60 to supply power to the first and second light sources 20 and 30.

The controller 10 may control on/off of a power supply, so the first light source 20 and the second light source 30 do not emit or emit light.

The controller 10 may control whether light is emitted from the first and second light sources 20 and 30, an amount of the light, the intensity of the light, or time in which the light is emitted. The controller 10 may control whether the light is emitted, an amount of the light, the intensity of the light, or timing at which the light is emitted, in various manners.

The power supply unit 60 is electrically connected with the first and second light sources 20 and 30 and the controller 10 to supply power to the first and second light sources 20 and 30 and the controller 10. Although drawings illustrate that the power supply unit 60 supplies power to the first and second light sources 20 and 30 and the controller 10, the present disclosure is not limited thereto. For example, the power supply unit 60 may be directly connected with the first and second light sources 20 and 30 to supply power to the first and second light sources 20 and 30.

The light irradiation apparatus 100 may further include an optical unit to selectively collect or radiate light emitted from the first and second light sources 20 and 30. The optical unit may include at least one lens, and the lens may perform various functions of focusing, dispersing, homogenizing, or non-homogenizing light from the first and second light sources 20 and 30.

In one or more embodiments of the present disclosure, an oxygenator may be selectively provided to the light irradiation apparatus 100. The oxygenator is connected with the controller 10 such that the oxygenator is turned on/off. When the oxygenator is turned on, oxygen is supplied to a target. A manner of supplying oxygen is not specified, and may include a manner of increasing the contact count with air by stirring a liquid using a stirrer, as well as a manner of providing oxygen to the target through a nozzle. For example, when light is irradiated to a specific fluid, at least one of the first and the second light may be irradiated to the fluid while stirring the fluid using the stirrer. Alternatively, when light is irradiated to a spot such as a skin of a human being, oxygen is supplied to the skin through a separate nozzle, which spurts oxygen, while at least one of the first light and the second light are being irradiated to the skin.

In one or more embodiments of the present disclosure, since the sterilization power is remarkably increased when oxygen is provided in irradiating light as described above, oxygen is smoothly provided into a cell in the case of, especially, 405-nm light. Accordingly, the production of the reactive oxygen species is promoted in the cell of the bacteria, thereby accelerating the destruction of the bacteria. In the present embodiment, the controller 10 simultaneously or individually drives the first light source 20 and the second light source 30. In other words, the first and second light sources 20 and 30 may be turned on/off simultaneously or individually. In addition, even the intensities of light, that is, the first light and the second light emitted from the first and second light sources 20 and 30 may be simultaneously or individually controlled.

A mode where each of the first light source 20 and the second light source 30 is powered on, is called an irradiation mode, and a mode where each of the first light source 20 and the second light source 30 is powered off, is called an idle mode, the first light source 20 and the second light source 30 are simultaneously turned on or turned off in one or more embodiments of the present disclosure. Accordingly, the duration that the first light source 20 operates in the irradiation mode may be completely identical to the duration that the second light source 30 operates in the irradiation mode. However, the durations, in which the first light source 20 and the second light source 30 are in the irradiation mode, are not limited thereto.

In one or more embodiments of the present disclosure, the controller 10 may control the intensity of light emitted from the first light source 20 and the second light source 30. The controller 10 may obtain a sterilizing effect specific to each target to be sterilized by adjusting type of a light to be irradiated to a target and an amount of irradiation energy for each light depending on a target to be sterilized.

For example, contents of photosensitizers vary depending on bacteria. Accordingly, a specific sterilization effect of a specific bacterium may be produced by adjusting an irradiation amount of first light to each bacterium. Since the second light induces the damage to substantially all DNAs or RNAs existing in bacteria, the sterilization effect may be produced with respect to all bacteria.

In one or more embodiments of the present disclosure, the controller 10 controls an amount of energy irradiated from the first light source 20 and the second light source 30. Particularly, the controller 10 may control an amount of energy irradiated from the first light source 20. The UV light represents an excellent sterilization effect, but the UV light may destroy a cell of a human body according to the same principle. In addition, the UV light may be applied to a normal skin cell to cause the damage to DNA, thereby causing skin cancer. For this reason, the UV light has excellent sterilization power, but health risks are high, so the UV has a limitation in use for a sterilization purpose. However, in one or more embodiments of the present disclosure, the controller 10 controls a daily irradiation amount to an extent that UV light is not harmful to the human body when controlling an amount of the UV light. Accordingly, the UV light may be applied to the human body.

To this end, in one or more embodiments of the present disclosure, the controller 10 may maintain a daily irradiation amount to 3 $mJ/cm^2$ or less in the case of ultraviolet light. In particular, in the case of UVC, the controller 10 maintains a daily irradiation amount to 3 $mJ/cm^2$ or less. In addition, in the case of UVA, when a daily irradiation time is less than 1000 seconds, an amount of UV irradiated may be maintained not to exceed 1 $J/cm^2$. When the daily irradiation time exceeds 1000 seconds, an amount of UV irradiated may be maintained not to exceed 1 $mW/cm^2$.

In one or more embodiments of the present disclosure, the first light may cause macular degeneration or may exert an influence on an eye due to the reduction of melatonin. Accordingly, the controller 10 may control a daily irradiation amount of light from the first light source 20 to a specific extent if necessary. However, the first light irradiated from the first light source 20 may correspond to a visible light region and may be applied to a target to be sterilized, which includes a human body, without the limitation in an additional irradiation amount of light. In addition, the controller 10 may prevent blue light from being excessively irradiated as a user wears glasses for blocking the blue light without controlling an amount of energy.

In one or more embodiments of the present disclosure, the distance from the first light source 20 and the second light source 30 to the target to be sterilized may be variously set. For example, the distance may be variously changed depending on the intensities of light from the first and second light sources 20 and 30, the type of a target to be sterilized, an area or a volume to be sterilized, or a target material (for example, germs or bacteria) to be sterilized. In one or more embodiments of the present disclosure, various settings for time in which light from the first light source 20 and the second light source 30 is irradiated may be available depending on the intensities of light from the first and second light sources 20 and 30, the type of a target to be sterilized, an area or a volume to be sterilized, or a target material (for example, germs or bacteria) to be sterilized.

In one or more embodiments of the present disclosure, the first and second light sources 20 and 30 may be implemented in the forms of various light sources to irradiate light in the above-described wavelength bands. For example, each of the first and second light sources 20 and 30 may independently use various light sources such as a light emitting diode, a halogen lamp, a fluorescent lamp, a gas discharge lamp, or a laser, without the limitation of types of light sources.

In one or more embodiments of the present disclosure, the first and second light sources 30 may be implemented with light emitting diodes. In other words, the first and second light sources 20 and 30 may be implemented with a light emitting diode to emit the first light and a light emitting diode to emit the second light.

Figure 2:
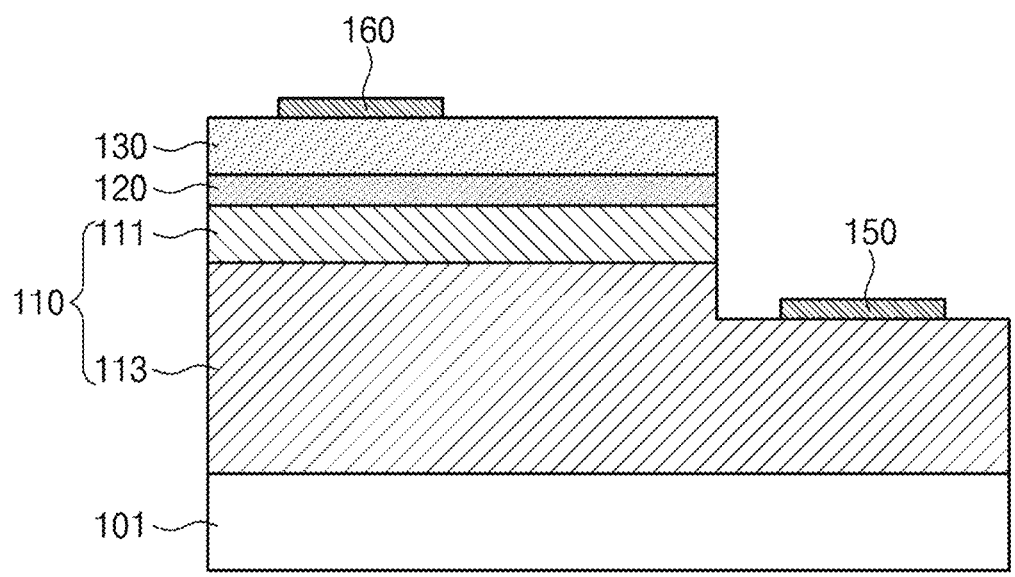
FIG. 2 is a cross-sectional view illustrating a light emitting diode, according to one or more embodiments of the present disclosure.

FIG. 2 is a cross-sectional view illustrating a light emitting diode, according to one or more embodiments of the present disclosure. However, the form of the light emitting diode is not limited thereto, but may be provided in various forms.

Referring to FIG. 2, according to one or more embodiments of the present disclosure, the light emitting diode may include a first semiconductor layer 110, an active layer 120, and a second semiconductor layer 130 sequentially provided on a semiconductor substrate 101.

The semiconductor substrate 101 is manufactured based on the above-description and becomes a growth substrate to grow the first semiconductor layer 110, the active layer 120, and the second semiconductor layer 130 thereafter.

The first semiconductor layer 110 is a semiconductor layer doped with a first conductive-type dopant. The first conductive-type dopant may be an n-type dopant. The first conductive-type dopant may be Si, Ge, Se, Te, or C.

In some embodiments, the first semiconductor layer 110 may include a nitride based semiconductor material. For example, the first semiconductor layer 110 may include a semiconductor material having a composition formula of $In_xAl_yGa_{1-x-y}N$ ($0 \leq x \leq 1$, $0 \leq y \leq 1$, $0 \leq x+y \leq 1$). In some embodiments, the semiconductor material having the above composition formula may include GaN, AlN, AlGaN, InGaN, InN, InAlGaN, and AlInN. The first semiconductor layer 110 may be formed in a growing manner of allowing the first semiconductor layer 110 to include an n-type dopant such as Si, Ge, Sn, Se, or Te by using the semiconductor material.

The first semiconductor layer 110 may include a first sub-semiconductor layer 111 having a higher impurity concentration and a second sub-semiconductor layer 113 having a lower impurity concentration. The first sub-semiconductor layer 111 may correspond to a contact layer connected with a first electrode 150 to be described below. The first sub-semiconductor layer 111 and the second sub-semiconductor layer 113 may be formed through sequential deposition, and may be formed by controlling deposition conditions. For example, the second sub-semiconductor layer 113 may be formed by performing deposition at a temperature lower than that of the first sub-semiconductor layer 111.

In some embodiments, the first semiconductor layer 110 may additionally have a structure in which two types of layers having mutually different band gaps are alternately stacked. The structure in which two types of layers having mutually different band gaps are alternately stacked may be a super lattice structure. Accordingly, in the first semiconductor layer 110, current spreading may be improved and stress may be relieved.

The two types of layers having mutually different band gaps may be alternately formed and include mutually different thin film crystal layers. In this case, when the two types of layers having mutually different band gaps are alternately stacked, the two types of layers may have a crystal lattice longer than a basic unit lattice, in a cyclic structure. The two types of layers having mutually different band gaps are a layer having a wide band gap and a layer having a narrow band gap. In one embodiment of the inventive concept, the layer having the wide band gap may be a $Al_xGa_yIn_{(1-x-y)}N$ ($0 \leq x < 1$, $0 < y \leq 1$) layer, and may be, for example, a GaN layer. The layer having the narrow band gap may be $Al_xGa_yIn_{(1-x-y)}N$ ($0 \leq x < 1$, $0 < y \leq 1$) and may be, for example, a $Ga_yIn_{(1-y)}N$ ($0 < y \leq 1$) layer.

In one embodiment of the inventive concept, at least one of the wide band gap layer and the narrow band gap layer may include an n-type impurity.

The active layer 120 is provided on the first semiconductor layer 110 and corresponds to a light emitting layer.

The active layer 120 is a layer which emits the light based on the band gap difference of the energy band resulting from the intrinsic material for the active layer 120 through the recombination of electrons (or holes) injected through the first semiconductor layer 110 and holes (or electrons) injected through the second semiconductor layer 130. The active layer 120 may emit at least one peak wavelength of UV light, blue light, green light, and red light.

The active layer 120 may be implemented with a compound semiconductor. The active layer 120 may be implemented with at least one of a group III-V compound semiconductor or a group II-VI compound semiconductor. The active layer 120 may employ a quantum well structure, and may have a multi-quantum well structure in which a quantum well layer and a barrier layer are alternately stacked. However, the structure of the active layer 120 is not limited thereto, and may include a quantum wire structure or a quantum dot structure.

In one or more embodiments of the present disclosure, the quantum well layer may be provided with a material having a composition formula of $In_xAl_yGa_{1-x-y}N$ ($0 \leq x \leq 1$, $0 \leq y \leq 1$, $0 \leq x+y \leq 1$). The barrier layer may be formed of a semiconductor material having a composition formula of $InxAl_yGa_{1-x-y}N$ ($0 \leq x \leq 1$, $0 \leq y \leq 1$, $0 \leq x+y \leq 1$) and may be provided with a composition ratio different from a composition ratio of the well layer. In this case, the barrier layer may have a band gap wider than a band gap of the well layer.

The well layer and the barrier layer may include, for example, at least one of pairs of AlGaAs/GaAs, InGaAs/GaAs, InGaN/GaN, GaN/AlGaN, AlGaN/AlGaN, InGaN/AlGaN, InGaN/InGaN, InGaP/GaP, AlInGaP/InGaP, and InP/GaAs. In some embodiments, the well layer of the active layer 120 may be implemented with InGaN, and the barrier layer of the active layer 120 may be implemented with an AlGaN-based semiconductor. In some embodiments, the indium composition of the well layer may be higher than the indium composition of the barrier layer, and the barrier layer may have no indium composition. In addition, the well layer does not include aluminum (Al), and the barrier layer may include aluminum (Al). However, the compositions of the well layer and the barrier layer are not limited thereto.

However, when the thickness of the well layer is excessively thin, the confinement efficiency of the carriers may be reduced, and when the thickness of the well layer is excessively thick, the carriers may be excessively confined. When the thickness of the barrier layer is excessively thin, the blocking efficiency of electrons may be reduced. When the thickness of the barrier layer is excessively thick, the electrons may be excessively blocked.

Accordingly, each carrier may be effectively confined in a well layer depending on the wavelength of light and the quantum well structure by appropriately adjusting the thickness of the barrier layer and the well layer.

In some embodiments, the thickness of each of well layers is not particularly limited, and the well layers may be equal or different thicknesses. When the well layers have equal thicknesses, the well layers have equal quantum levels, so the well layers may have the same light emitting wavelength. In this case, an emission spectrum having a narrow half width may be obtained. When the thicknesses of the well layers are different, the emission wavelengths in the well layers may be varied, thereby increasing the emission spectrum.

In some embodiments, at least one of the plurality of barrier layers may include a dopant, and may include at least one of n-type and p-type dopants. The barrier layer may be an n-type semiconductor layer when the batter layer is doped with the n-type dopant. When the barrier layer is the n-type semiconductor layer, the injection efficiency of electrons injected into the active layer 120 may be increased.

In some embodiments, the barrier layer may have various thicknesses, but the uppermost barrier layer may have a thickness equal to or greater than those of other barrier layers.

When the active layer 120 has a multi-quantum well structure, the composition of a quantum well layer and a barrier layer may be set depending on a light emitting wavelength required for the light emitting diode. In some embodiments, the compositions of a plurality of well layers may be the same or may not be the same. For example, impurities may be contained in a lower well layer, but may not be contained in an upper well layer.

The second semiconductor layer 130 is provided on the active layer 120.

The second semiconductor layer 130 is a semiconductor layer doped with a second conductive-type dopant having a polarity opposite to that of the first conductive-type dopant. The second conductive-type dopant may be a p-type dopant, and the second conductive-type dopant may include, for example, Mg, Zn, Ca, Sr, or Ba.

In one or more embodiments of the present disclosure, the second semiconductor layer 130 may include a nitride based semiconductor material. The second semiconductor layer 130 may include a semiconductor material having a composition formula of $In_xAl_yGa_{1-x-y}N$ ($0 \leq x \leq 1$, $0 \leq y \leq 1$, $0 \leq x+y \leq 1$). In some embodiments, the semiconductor material having the composition formula may include GaN, AlN, AlGaN, InGaN, InN, InAlGaN, or AlInN. The second semiconductor layer 130 may be formed in a growing manner of allowing the second semiconductor layer 130 to include a p-type dopant such as Mg, Zn, Ca, Sr, or Ba by using the semiconductor material.

In some embodiments, the first electrode 150 and the second electrode 160 are provided on the first semiconductor layer 110 and the second semiconductor layer 130, respectively. Particularly, some of the second sub-semiconductor layer 113, the active layer 120, and the second semiconductor layer 130 may be removed, and thus, a part of the first sub-semiconductor layer 111 may be exposed. The first electrode 150 may be provided on the first sub-semiconductor layer 111. The second electrode 160 may be provided on the second semiconductor layer 130.

In some embodiments, the light emitting diode may emit the first light and the second light according to one or more embodiments of the present disclosure by setting the material constituting each layer and the type of impurity contained in each layer, and setting the thickness of each layer to specific values.

According to one or more embodiments of the present disclosure, the following effects may be obtained by using a light emitting diode instead of an existing typical lamp as a light source to apply light to a test sample.

When the light emitting diode is used as the light source according to one or more embodiments of the present disclosure, light having a specific wavelength may be provided to an irradiation target, as compared to light emitted from the existing typical lamp (for example, an existing UV lamp). The light emitted from the existing lamp has a broader spectrum in a wider area as compared to the light emitted from the light emitting diode. Accordingly, in the case of the existing UV lamp, it is not easy to separate only light having some band of the wavelength band of the emitted light. In contrast, the light emitted from the light emitting diode has a sharp peak at a specific wavelength and provides light of a specific wavelength having a very small half-width as comparison to light from an existing lamp. Accordingly, it is easy to select light of a specific wavelength and only the selected light of the specific wavelength may be provided to a test sample.

In addition, in the case of the existing lamp, although light is provided to the test sample, it may be difficult to precisely limit an amount of light. However, in the case of the light emitting diode, light may be provided by exactly limiting the amount of light. Further, in the case of the existing lamp, since it may be difficult to precisely limit the amount of light, the irradiation time may also be set in a wide range. However, in the case of the light emitting diode, light necessary for the test sample may be provided within a definite time for a relatively short time.

As described above, in the case of the conventional lamp, it is difficult to clearly determine the light irradiation amount due to the relatively wide range of wavelengths, the wide range of light quantity, and the wide range of irradiation time. To the contrary, the light emitting diode can provide a clear light irradiation amount due to a relatively narrow range of wavelengths, a narrow amount of light, and a narrow range of irradiation time.

In addition, in the case of the existing lamp, it takes longer time to arrive at the maximum amount of light after power is turned on. To the contrary, when the light emitting diode is used, an amount of light instantly arrives at the maximum amount of light since warming-up time is hardly taken after the power is turned on. Therefore, in the case of a light source employing the light emitting diode, the irradiation time of the light may be clearly controlled when irradiating light of a specific wavelength to an optical element target.

Figure 3A:
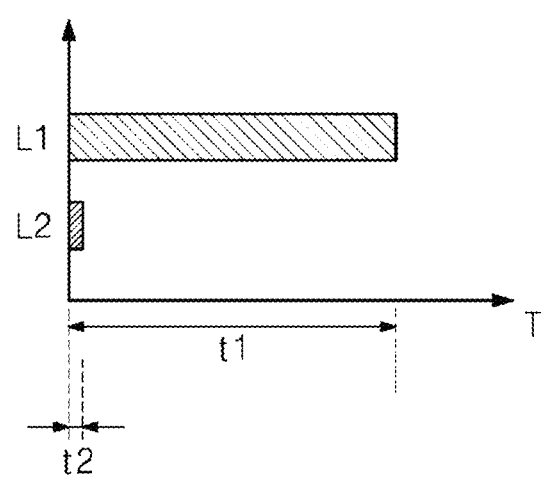
FIGS. 3A to 3C illustrate a method for driving a light irradiation apparatus, according to one or more embodiments of the present disclosure, and illustrates times based on turning on/off the first and second light sources.
Figure 3B:
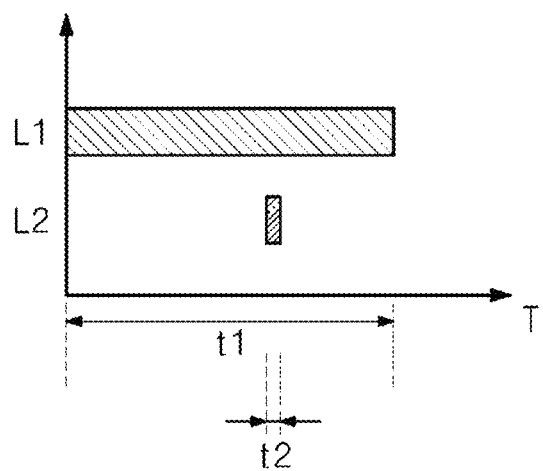
Figure 3C:
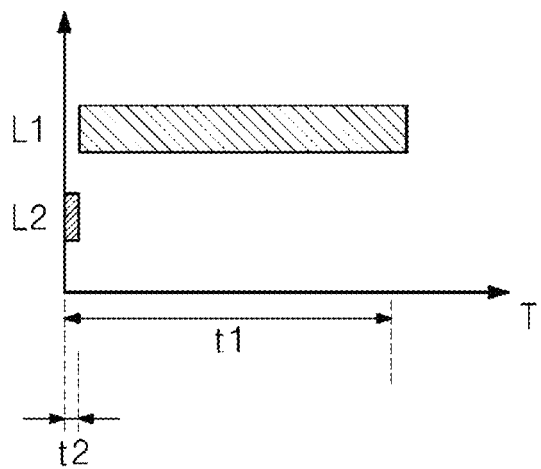

FIGS. 3A to 3C illustrate a method for driving a light irradiation apparatus, according to one or more embodiments of the present disclosure, and illustrates times based on turning on/off the first and second light sources.

According to one or more embodiments of the present disclosure, in the light irradiation apparatus, the first light is assigned with "L1", the second light is assigned with "L2", and elapsed time is assigned with "T", the first light source is turned on for a first time t1 to emit the first light L1, and the second light source is turned on for a second time t2 to emit the second light L2. In the present embodiment, the first time t1 in which the first light L1 is irradiated may be longer than the second time t2 in which the second light L2 is irradiated. Since the second light L2 exerts a great influence on, especially, a human body, the second light L2 may be irradiated for a shorter time than the irradiation time of the first light L. For example, the first light L1 may be applied for about 10 minutes, and the second light L2 may be applied for less than about 10 seconds.

The irradiation times t1 and t2 of the first light L1 and the second light L2 emitted from the first and second light sources 20 and 30, and amounts of the first light L1 and the second light L1 in irradiation may be variable, but a total dose applied to a target to be sterilized may be set to a value harmless to the human body. In particular, a dose per day, which is in a harmless range, is an allowable dose when the second light L2 is applied to the human body, the second light source 30 may emit the second light L2 in less than the allowable dose. The dose may vary depending on the harmfulness of the light emitted from the first light source 20 and the second light source 30. In one or more embodiments of the present disclosure, the dose of the second light source 30 may be less than 1/10 of the dose of the first light source 20, and, according to another embodiment, may be 1/20 of the dose of the first light source 20. For example, the allowable dose of the second light L2 may be in the range of about 30 $J/m^2$ to about 1,000,000 $J/m^2$.

As illustrated in FIG. 3A and FIG. 3C, the first light L1 and the second light L2 may be started to be irradiated simultaneously or at mutually different times. When the first light L1 and the second light L2 may be started to be irradiated at mutually different times, the first light L1 may be first irradiated or the second light L2 may be first irradiated. The times in which the first light L1 and the second light L2 are irradiated may be overlapped with each other or not overlapped with each other. When the times, in which the first light L1 and the second light L2 are irradiated, are not overlapped with each other, the interval between the times in which the first light L1 and the second light L2 are applied may be set to be a shorter time interval. For example, the interval between the times in which the first light L1 and the second light L2 are applied may be within several times, several minutes, or several seconds.

The sterilizing device according to one or more embodiments of the present disclosure exhibits a sterilization effect higher than the individual sterilization effect by the first light L1 or the individual sterilization effect by the second light L2, due to the synergy effect that may be obtained as the first light and the second light are applied simultaneously or within times close to each other.

According to one or more embodiments of the present disclosure, the sterilizing device employs the sterilization principle of the first light of generating reactive oxygen species due to a photosensitizer and the second light of causing the damage to DNA by obtaining a thymine dimer. In one or more embodiments of the present disclosure, the significantly high sterilization effect may be obtained within a shorter time even with a smaller amount of energy when the mixture of the first light source and the second light source is used, as compared to the case of an individual use of the first and second light sources The bacteria having received chemical and physical stresses may be rapidly increased in a death rate even by a weak stimulus additionally applied thereto. Accordingly, in one or more embodiments of the present disclosure, mutually different two sterilizing mechanisms based on the first light and the second light, which correspond to blue light and UV light, apply mutually different stresses to the bacteria. Accordingly, the synergy effect of the stresses may destroy the bacteria with a smaller amount of energy as compared to the individual use of the two light sources. According to one or more embodiments of the present disclosure, the second light is irradiated in amount harmless to a biological tissue of a target to be sterilized, while being applied together with the first light. Accordingly, the sterilization synergy effect may be obtained by two light sources, so the present disclosure may produce the effective sterilization effect within a shorter time without the damage to a human tissue, when the target to be sterilized is a human body.

To the contrary, the use of only the first light is not harmful to the human body, but the sterilization power is weak. Accordingly, the first light needs to be irradiated with higher energy for a longer time. It should be noticed that the use of only the second light produces excellent sterilization power, but the second light is harmful to the human body.

As described above, in one or more embodiments of the present disclosure, the light irradiation apparatus may be used to sterilize various pathogens. Particularly, according to one or more embodiments of the present disclosure, the light irradiation apparatus 100 may be used for sterilizing infectious bacteria in the initial stage by irradiating sterilizing light to an acute infected wound, and thus, the period for curing the wound may be shortened. For the acute wound, reducing the number of infectious bacteria in the initial stage of the wound is the most important in the process of curing the wound. When the initial sterilization is not sufficient performed with respect to the acute wound, the curing of the cut is no performed normally, so a cut may develop into a chronic cut that is not cured for 3 months or longer. However, when the infectious bacteria are sterilized in the initial stage using the light irradiation apparatus 100 according to the embodiment of the present disclosure, the chronic cut may be prevented.

In addition, microorganisms, such as bacteria, germs, and molds, present on animals and various articles may be sterilized in addition to the human body. Accordingly, the target to be sterilized by the sterilizing device according to one or more embodiments of the present disclosure is not limited to a human body, but may be expanded to animals and various articles.

According to the embodiment of the present disclosure as described above, the sterilization effect may be significantly increased when the first light and the second light emitted from the first light source 20 and the second light source 30 are applied simultaneously or within times close to each other. In addition, according to one or more embodiments of the present disclosure, when the first light and the second light are sequentially irradiated, the significantly higher sterilization effect may be obtained as compared to that the second light and the first light are sequentially irradiated. Accordingly, according to one or more embodiments of the present disclosure, the sterilization effect may be maximized through sequentially applying the first light and the second light to the target to be sterilized.

According to one or more embodiments of the present disclosure, the first light is applied to the target to be sterilized for a specific time before the second light is irradiated, and then the second light is irradiated. Accordingly, DNA is prevented from being recovered from the damage again after the first light is first irradiated. Accordingly, the significantly higher sterilization effect may be obtained even with a smaller dose as compared to the case that the first light is individually irradiated.

In one or more embodiments of the present disclosure, when the second light is emitted sequentially in addition to the first light, in addition to the first light, an amount of the second light needs to be controlled. In one or more embodiments of the present disclosure, the synergy effect of sterilization may be obtained and an influence on the human body may be minimized by sequentially irradiating the first light and the second light. To this end, when the first light source 20 and the second light source 30 are turned on/off, a manner of continuously emitting light, a manner of sequentially increasing or decreasing the intensity of light, a flickering manner, or a manner of mixing the above manners may be employed.

Figure 4A:
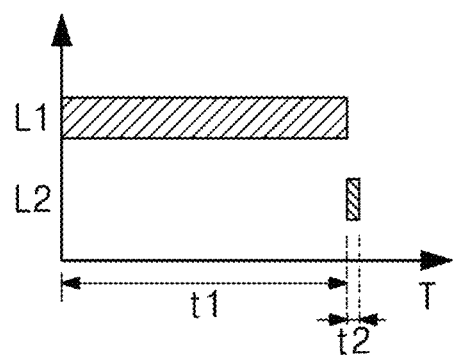
FIGS. 4A and 4B are views illustrating a method for driving a light irradiation apparatus, according to one or more embodiments of the present disclosure, when first light and second light are sequentially irradiated, and illustrates times based on turning on/off the first and second light sources.
Figure 4B:
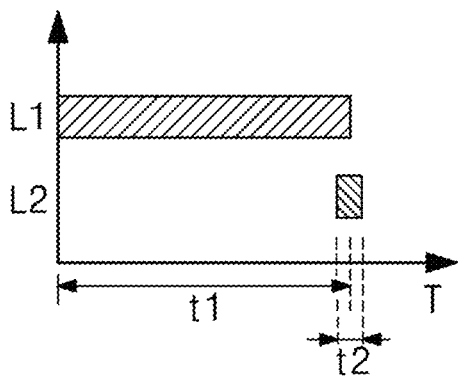

FIGS. 4A and 4B are views illustrating a method for driving a light irradiation apparatus, according to one or more embodiments of the present disclosure, when first light and second light are sequentially irradiated, and illustrates times based on turning on/off the first and second light sources.

Referring to FIGS. 4A and 4B, in one or more embodiments of the present disclosure, the first light L1 may be first irradiated, and then the second light L2 may be irradiated. When the first light L1 is first irradiated and then the second light L2 is irradiated, the sterilization effect is significantly increased as compared to the case that the second light is first irradiated and then the first light L1 is irradiated. When the second light L2 is first irradiated and the first light L1 is later irradiated, the effect of inhibiting the proliferation of bacteria by the second light L2 may be reduced by irradiating the first light L. Accordingly, even if the structure of DNA is partially mutated by the second light L2, the mutated DNA is subject to photoreactivation by irradiating the first light L. The bacteria recovered through the irradiation of the first light L1 return to a state in which the bacteria may be proliferated. Accordingly, although the total sterilization power is still excellent, the sterilization power in the final stage may be more reduced as compared to the case that the first light L1 and the second light L2 are sequentially irradiated.

Alternatively, when the first light L1 is applied to the target to be sterilized and then the second light L2 is sequentially applied to the target to be sterilized by using the light irradiation apparatus 100 according to one or more embodiments of the present disclosure, reactive oxygen species are produced in bacteria by the first light L1, which is first irradiated, so oxidative stress is caused in bacteria. In this state, since additional sterilization is performed by the second light L2 irradiated later, the death rate of the bacteria is significantly increased even in a smaller irradiation amount.

In this embodiment, the time point at which the second light L2 is applied may vary under the condition that the first light L1 and the second light L2 are sequentially applied. For example, irradiation of the second light L2 may start after the irradiation of the first light L1 is completed as illustrated in FIG. 3A, and as illustrated in FIG. 3B, the irradiation of the second light L2 may start even though the irradiation of the first light L1 is not completed. In this case, since time points at which the first light L1 and the second light L2 are irradiated may be partially overlapped with each other, the first time and the second time may have mutually overlap durations.

As described above, the light irradiation apparatus according to one or more embodiments of the present disclosure may be driven by the controller under the condition that the first light L1 and the second light L2 are sequentially irradiated.

Figure 5A:
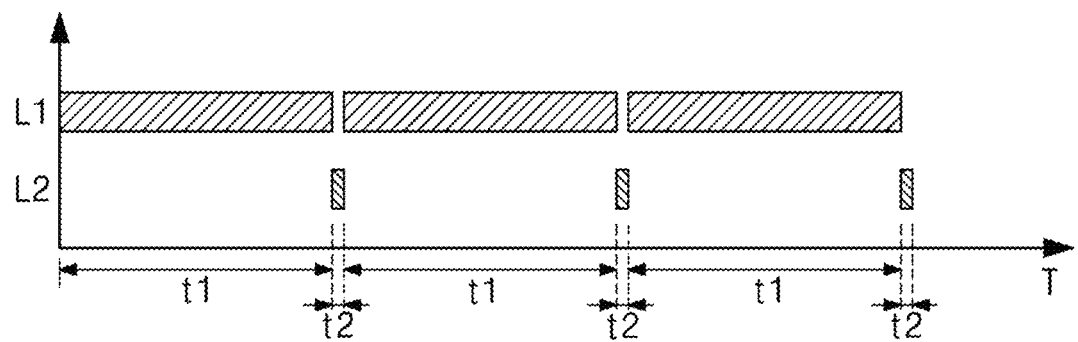
FIGS. 5A to 5C illustrate a method for driving a light irradiation apparatus, according to one or more embodiments of the present disclosure, and illustrates times based on turning on/off the first and second light sources.
Figure 5B:
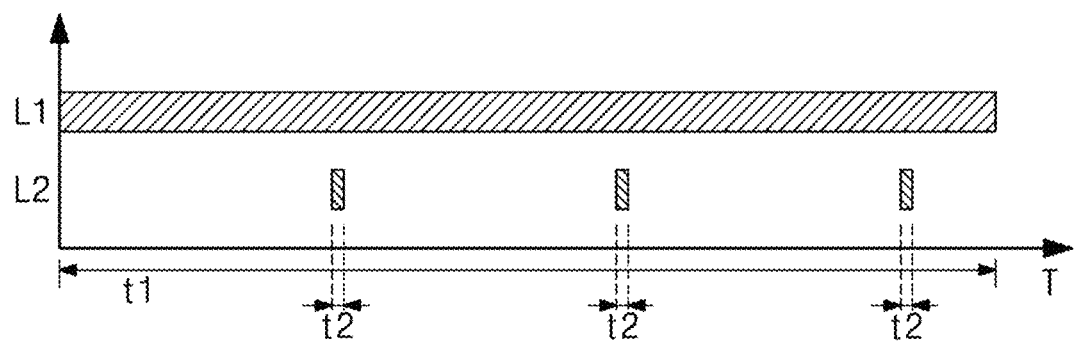
Figure 5C:
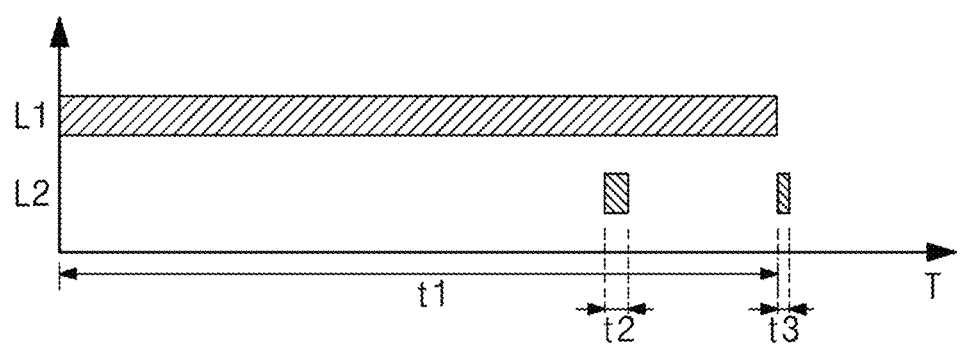

FIGS. 5A to 5C illustrate a method for driving a light irradiation apparatus, according to one or more embodiments of the present disclosure, and illustrates times based on turning on/off the first and second light sources.

Referring to FIG. 5A, the first light L1 and the second light L2 may be periodically irradiated to the target to be sterilized. In other words, the first light L1 is irradiated to the target to be sterilized for the first time t1, and the second light L2 is irradiated to the target to be sterilized for the second time t2. Then, irradiation of the first light L1 and the second light L2 is repeated. The repeat period and the repeat count may vary depending on the type of the target to be sterilized and the total amount of the target to be sterilized. In this case, the repeat period and the repeat count of the first light L1 and the second light L2 may be determined such that the total dose of the first light L1 and the total dose of the second light L2 become values equal to or less than the allowable dose for the human body.

Referring to FIG. 5B, when the first light L1 and the second light L2 are applied, the first light L1 may be continuously applied to the target to be sterilized without interruption under the condition that the second light L2 is applied after the first light L1 is applied. To the contrary, the second light L2 is not continuously applied, but discontinuously applied while being superposed with the first light L1.

As illustrated in drawings, the first light L1 may be continuously applied to the target to be sterilized for the first time t1 without interruption, and the second light L2 may be applied to the target to be sterilized for the second time t2 during the continuous application of the first light L1, after the first light L1 is applied to some extent. The second light L2 may be continuously repeatedly applied to the target to be sterilized.

Referring to FIG. 5C, when the first light L1 and the second light L2 are applied, the first light L1 may be continuously applied to the target to be sterilized without interruption or may stop before the second light L2 is applied, under the condition that the second light L2 is applied after the first light L1 is applied. As illustrated in drawings, when the first light L1 is applied to the target to be sterilized for the first time t1, the second light L2 may be applied for the second time t2 during the application of the first light L. Thereafter, after the application of the first light L1 is finished, the second light L2 may be applied for a third time t3. In this case, regarding the application time of the second light L2, the second light L2 may be applied to the target to be sterilized for mutually different time within an allowable dose permitted as being safe (no health risk) for a human body. In other words, the second time t2 and the third time t3 in which the second light L2 is applied may have mutually different values.

In one or more embodiments of the present disclosure, when the second light L2 is instantly applied as soon as the first light L1 is applied and stopped, the highest sterilization effect may be obtained, and the second light L2 may be sequentially applied without interruption in the state the first light L1 is applied. However, instead of that the second light L2 is instantly applied as soon as the first light L1 is applied and stopped, time may be slightly elapsed, and then the second light L2 may be applied. In this case, the elapsed time interval may be significantly short. Meanwhile, when the sterilization effect is obtained as the first light L1 and the second light L2 are sequentially applied, the next sequential irradiation of the first light L1 and the second light L2 may be performed after a sufficient amount of time is elapsed.

According to one or more embodiments of the present disclosure, the light irradiation apparatus may be implemented in various forms.

Figure 6A:
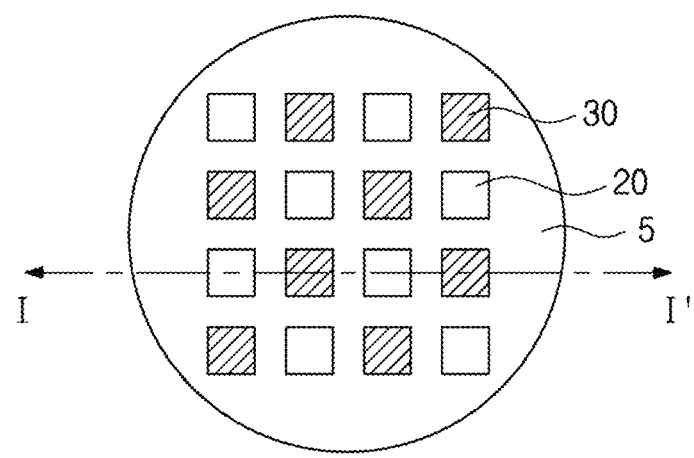
FIG. 6A is a plan view of the light irradiation apparatus according to one or more embodiments of the present disclosure.
Figure 6B:
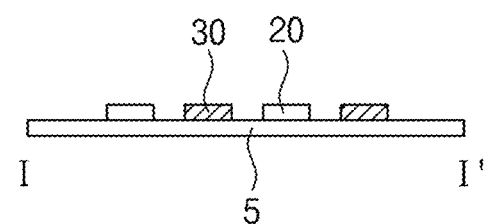
FIG. 6B is a sectional view taken along line I-I' of FIG. 6A.

FIG. 6A is a plan view of the light irradiation apparatus according to one or more embodiments of the present disclosure, and FIG. 6B is a sectional view taken along line I-I' of FIG. 6A.

Referring to FIGS. 6A and 6B, according to one or more embodiments of the present disclosure, the light irradiation apparatus may include the first light source 20, the second light source 30, and the substrate 5 on which the first light source 20 and the second light source 30 are mounted.

In the present embodiment, a plurality of first light sources 20 may be provided, and a plurality of second light sources 30 may be provided. For example, the first light sources 20 and the second light sources 30 may be provided in equal numbers and may be alternately arranged in the form of a matrix as illustrated in the drawing. However, the number of the first and second light sources 20 and 30 is not limited thereto, and the number of the first light sources 20 may be larger than or smaller than the number of the second light sources 30. In addition, according to one or more embodiments of the present disclosure, the first light sources 20 and the second light sources 30 may be regularly or irregularly arranged depending on the number of the first light sources 20 and the number of the second light sources 30.

According to one or more embodiments of the present disclosure, the light irradiation apparatus 100 may further include a housing to receive the first and second light sources 20 and 30 and the substrate 5. The housing may have a transmission window to transmit light emitted from the first and second light sources 20 and 30 and the light emitted from the first and second light sources 20 and 30 may be provided to the human body through the transmission window.

In one or more embodiments of the present disclosure, the controller 10 may be provided in various forms on the substrate 5. For example, the controller 10 may be provided in the form of a separate circuit wiring or in the form of a separate chip, to be mounted on the substrate 5.

In some embodiments, the light irradiation apparatus may obtain the sterilization effect significantly higher than each of the sterilization effect obtained from the first light and the sterilization effect obtained from the second light, through synergy that may be obtained by simultaneously applying the first light and the second light.

According to one or more embodiments of the present disclosure, the light irradiation apparatus employs the sterilization principle of the first light of generating cytotoxic reactive oxygen species due to a photosensitizer and the second light of causing the damage to DNA by producing the pyrimidine dimer. In one or more embodiments of the present disclosure, the significantly high sterilization effect may be obtained within a shorter time even with a smaller amount of energy by using the mixture of the first light source and the second light source, as compared to the case of an individual use of the first light source and the second light source.

The bacteria having chemical and physical stresses may be rapidly increased in a death rate even by a weak stimulus additionally applied thereto. Accordingly, in one or more embodiments of the present disclosure, mutually different two sterilizing mechanisms based on the first light and the second light, which correspond to blue light and UV light, apply mutually different stresses to the bacteria. Accordingly, the synergy effect of the stresses may destroy the bacteria with a smaller amount of energy as compared to the individual use of the two light sources.

According to one or more embodiments of the present disclosure, the second light is irradiated in amount harmless to a biological tissue of the target to be sterilized while being applied together with the first light. Accordingly, the sterilization synergy effect may be produced by two light, so the present disclosure may obtain the effective sterilization effect within a shorter time without the damage to the human tissue, when the target to be sterilized is a human body.

To the contrary, the use of only the first light is not harmful to the human body, but the sterilization power is weak, so the first light needs to be irradiated with higher energy for a longer time. The use of only the second light may produce excellent sterilization power, but harmful to the human body.

The light irradiation apparatus may be implemented in various forms and used for various purposes. For example, according to one or more embodiments of the present disclosure, the light irradiation apparatus may be applied to various places requiring lighting and sterilizing, and may be used as a special lighting device. For example, the light irradiation apparatus may be used in medical facilities such as operating rooms or hospitals or used as a lighting device for public hygiene or personal hygiene. In particular, according to one or more embodiments of the present disclosure, the light irradiation apparatus 100 may be used for treating a patient.

According to the present disclosure, the light irradiation apparatus may be applied to public facilities, a community use space, and products for common use for treatment purposes, or may be applied to private facilities, a private space, and a persona use product for treatment purposes.

As described above, according to one or more embodiments of the present disclosure, the sterilizing device may be applied to various other devices requiring sterilizing, and particularly, may be applied to a device using a light source. In addition, the sterilizing device may be used as a lighting device in addition to the intrinsic function thereof. For example, according to one or more embodiments of the present disclosure, the sterilizing device may further include an additional light source for lighting a specific space. In this case, the additional light source may emit light in a visible wavelength band. The additional light source may emit light corresponding to the entire spectrum of the visible light area, or may emit light corresponding to the spectrum of a specific color.

Alternatively, in one or more embodiments of the present disclosure, the first light source 20 may emit light in the visible light wavelength band including light in the blue wavelength band without an additional light source. For example, the first light source 20 emits light in a wavelength band in the range of about 380 nm to about 750 nm, and most of the light corresponds to a visible light wavelength band. In this case, the first light source 20 may totally provide light in the visible light wavelength band while providing light in the blue wavelength band for obtaining a synergic effect through the combination with the second light source 30, thereby obtaining the sterilization effect as in embodiments described above. In this manner, when an additional light source is provided to emit light in the visible light wavelength band or the first light source emits the light in the visible light wavelength band, the light may have the spectrum similar to that of sunlight. The light having the spectrum similar to that of sunlight may exhibit the effect similar to being frequently exposed to sunlight. Accordingly, the synthesis of vitamin D may be facilitated or the prevalence ratio of illnesses such as nearsightedness may be lowered.

Hereinafter, an experimental example of the sterilization effect of the light irradiation apparatus according to one or more embodiments of the present disclosure will be described.

Figure 7:
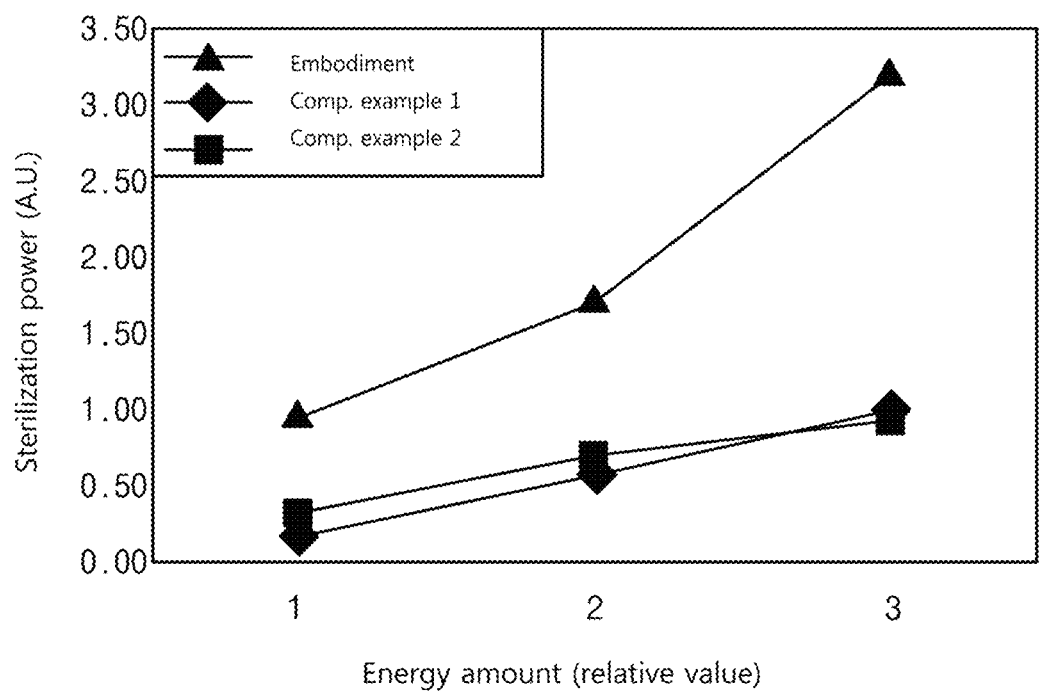
FIG. 7 is a graph illustrating an experimental result on the sterilization effect of the light irradiation apparatus, according to one or more embodiments of the present disclosure.

Experimental Example 1—Sterilization Power Test 1 of First Light and Second Light FIG. 7 is a graph illustrating an experimental result on the sterilization effect of the light irradiation apparatus, according to one or more embodiments of the present disclosure.

In FIG. 7, Embodiment indicates sterilization power obtained by using the sterilizing device according to one or more embodiments of the present disclosure. A light source to emit blue light having the wavelength of 405 nm was used as the first light source, and a light source to emit UV light having the wavelength of 225 nm was used as the second light source.

Comparative Example 1 shows the sterilization power when only the first light source is used, in which light having the wavelength of 405 nm was used. Comparative Example 2 shows the sterilization power when only the second light source is used, in which light having the wavelength of 225 nm was used.

The target to be sterilized was *Staphylococcus aureus*. *Staphylococcus aureus* is a gram-positive tuberous anaerobic bacterium and is present in a large number inside the nasal cavity and skin of a human body. *Staphylococcus aureus* is a bacterium most often causes food poisoning except for *salmonella* and enteritis *vibrio*. Recently, methicillin-resistant *Staphylococcus aureus* (MRSA), which is a strain showing resistance to antibiotics, has appeared and corresponds to a main target to be sterilized.

*Staphylococcus aureus* was prepared in the form of a suspension at a constant concentration after cultured, and light of each of Embodiment, Comparative Example 1, and Comparative Example 2 was irradiated to a respective suspension. The respective suspension irradiated with the light of each of Embodiment, Comparative Example 1, and Comparative Example 2 was diluted to a constant concentration, was inoculated on an agar plate, and was cultured. Thereafter, the number of colonies of cultured strains was determined, was converted into a log value, and was marked as sterilization power in a graph. In this case, when the light of each of Embodiment, Comparative Example 1 and Comparative Example 2 is irradiated to the respective suspension, the light was irradiated by increasing only an amount of energy two times or three times while maintaining the same condition. Accordingly, an amount of energy for each light was expressed as "1", "2", and "3". In this case, the maximum irradiation amount of Comparative Example 2 of energy is maintained not to exceed 3 mJ/cm$^2$.

The following Table 1 shows data obtained by expressing the sterilization power illustrated in FIG. 7 as numeric values.

TABLE 1

| An amount of energy (relative value) | 1 | 2 | 3 |
|---|---|---|---|
| Embodiment | 0.19 | 0.56 | 0.98 |
| Comparative Example 1 | 0.29 | 0.69 | 0.94 |
| Comparative Example 2 | 0.29 | 0.69 | 0.94 |

As recognized in Table 1 and FIG. 7, the sterilizing device according to one or more embodiments of the present disclosure shows higher sterilization power than those of Comparative Example 1 of irradiating only blue light and Comparative Example 2 of irradiating only UV light. This means that there is a synergic effect for the sterilization power when the mixture of blue light and UV light is used as in the present disclosure, as compared to a sterilizing device individually using only blue light or only UV light.

In this case, an amount of light is determined depending on the intensity of light and time. Accordingly, it may be understood that a smaller amount of energy is required to obtain the same sterilization power, as compared to Comparative Example 1 or Comparative Example 2, which represents that the irradiation time is reduced under the same luminous intensity.

Figure 8:
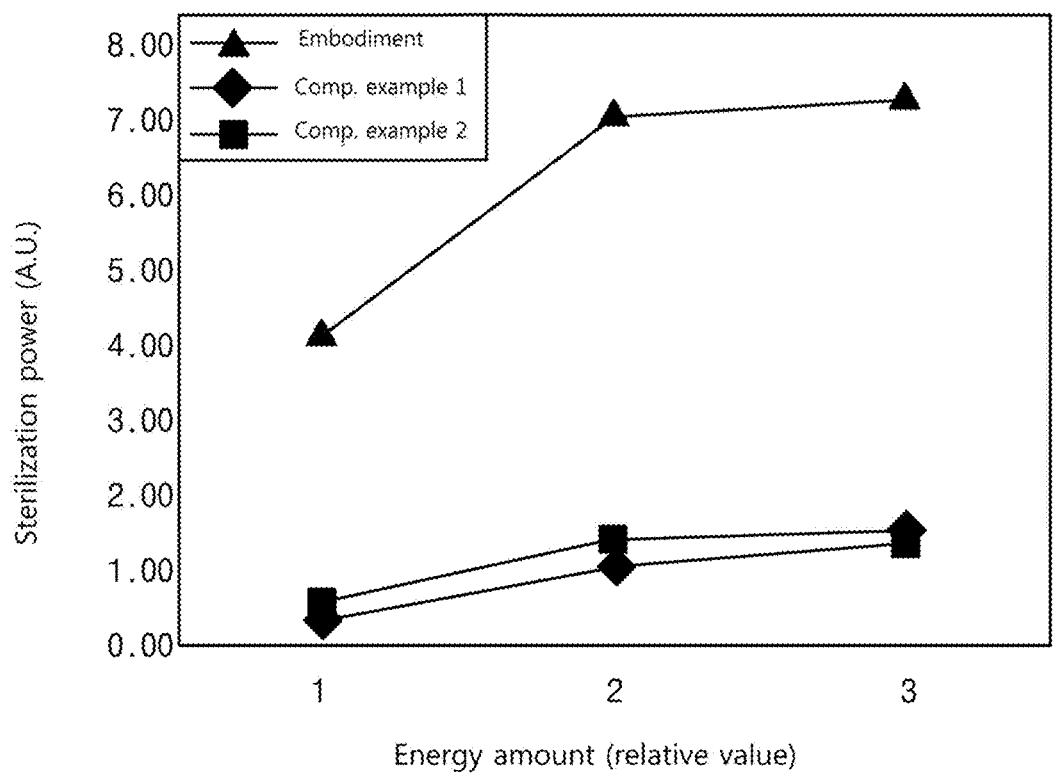
FIG. 8 is a graph illustrating an experimental result on the sterilization effect of the light irradiation apparatus, according to one or more embodiments of the present disclosure.

Experimental Example 2—Sterilization Power Test 2 in Combination of First Light and Second Light FIG. 8 is a graph illustrating an experimental result on the sterilization effect of the sterilizing device according to one or more embodiments of the present disclosure.

In FIG. 8, a curve marked as "Embodiment" represents sterilization power of the sterilizing device according to one or more embodiments of the present disclosure. A light source to emit blue light having the wavelength of 405 nm was used as the first light source, and a light source to emit UV light having the wavelength of 275 m was used as the second light source.

Comparative example 1 shows sterilization power when only the first light source is used, in which a light source to emit light having the wavelength of 405 nm was used. Comparative example 2 shows sterilization power when only the second light source is used, in which a light source to emit light having the wavelength of 275 nm was used.

A target to be sterilized was *Staphylococcus aureus*, and each experiment was performed five times under the same condition.

In the present experiment, the procedure of measuring the sterilization power after cultivating *Staphylococcus aureus* was the same as that described with reference to FIG. 7.

The following Table 2 shows data obtained by expressing the sterilization power, which is illustrated in FIG. 8, as a numeric value.

TABLE 2

| Energy amount (relative value) | 1 | 2 | 3 |
|---|---|---|---|
| Embodiment | 4.76 | 6.88 | 7.00 |
| Comparative Example 1 | 0.69 | 1.29 | 1.53 |
| Comparative Example 2 | 0.50 | 1.05 | 1.40 |

As recognized in Table 2 and FIG. 8 the sterilizing device according to one or more embodiments of the present disclosure shows significantly high sterilization power as compared to Comparative Example 1 that only blue light is irradiated and Comparative Example 2 that only UV light is irradiated. In particular, the sterilizing device according to one or more embodiments of the present disclosure shows significantly high sterilization power as compared to Comparative Example 1 and Comparative Example 2 of irradiating only blue light and only UV light, respectively throughout the whole duration regardless of an amount of energy. In addition, the light irradiation apparatus according to one or more embodiments of the present disclosure shows the tendency that the sterilization power is increased as an amount of energy is increased.

This means that there is a synergic effect for the sterilization power when the mixture of blue light and UV light is used as in the present disclosure, as compared to a sterilizing device individually using only blue light or only UV light.

Figure 9:
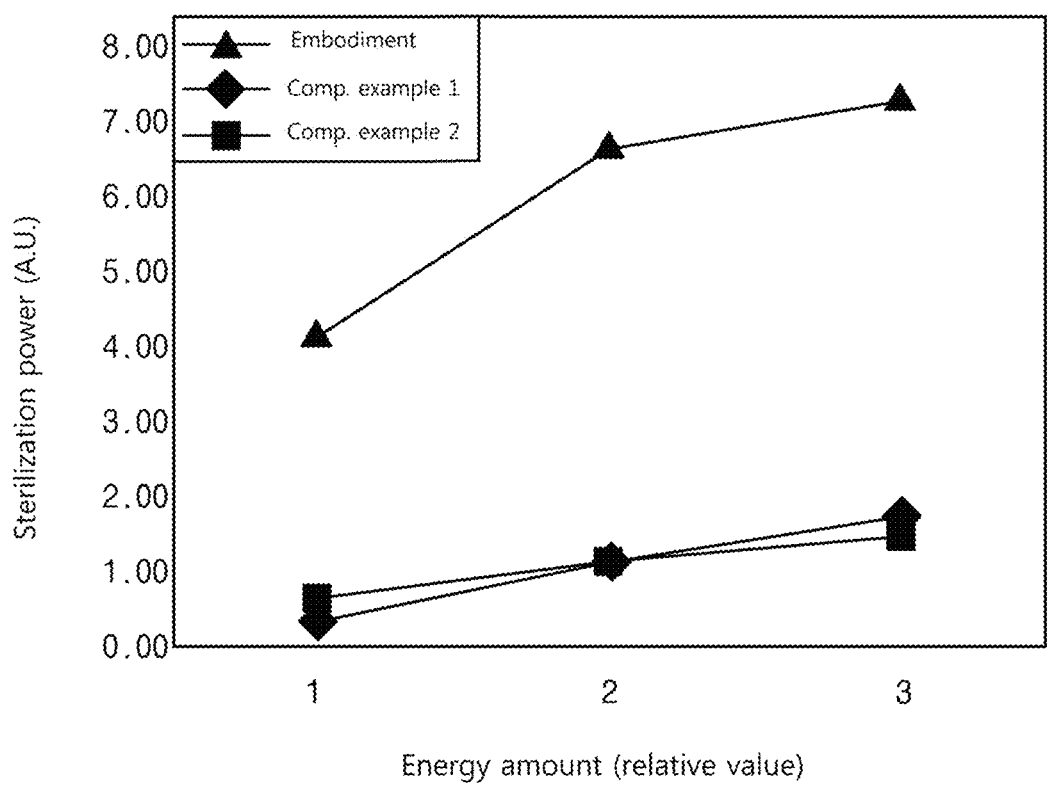
FIG. 9 is a graph illustrating an experimental result on the sterilization effect of Colon *bacillus* in the light irradiation apparatus according to one or more embodiments of the present disclosure.

Experimental Example 3—Sterilization Power Test 3 of First Light and Second Light FIG. 9 is a graph illustrating an experimental result on the sterilization effect of the sterilizing device according to one or more embodiments of the present disclosure.

In FIG. 9, Embodiment indicates sterilization power obtained by the sterilizing device according to one or more embodiments of the present disclosure. A light source to emit blue light having the wavelength of 405 nm was used as the first light source, and a light source to emit UV light having the wavelength of 275 nm was used.

Comparative example 1 shows sterilization power when only the first light source is used, in which a light source to emit light having the wavelength of 405 nm was used. Comparative example 2 shows sterilization power when only the second light source is used, in which a light source to emit light having the wavelength of 275 nm was used.

A target to be sterilized was colon *bacillus*, and each experiment was performed five times under the same condition. In the present experiment, the procedure of measuring the sterilization power after cultivating colon *bacillus* was the same as that described with reference to FIG. 7.

The following Table 3 shows data obtained by expressing the sterilization power illustrated in FIG. 8 as numeric values.

TABLE 3

| An amount of energy (relative value) | 1 | 2 | 3 |
|---|---|---|---|
| Embodiment | 4.23 | 6.57 | 7.00 |
| Comparative Example 1 | 0.53 | 1.35 | 1.93 |
| Comparative Example 2 | 0.77 | 1.26 | 1.63 |

As recognized from table 3 and FIG. 9, the sterilizing device according to one or more embodiments of the present disclosure shows higher sterilization power than the sterilization power of Comparative Example 1 of irradiating only blue light to colon *bacillus* as well as *Staphylococcus aureus* and the sterilization power of Comparative Example 2 of irradiating only UV light to colon *bacillus* as well as *Staphylococcus aureus*. In particular, the sterilizing device according to one or more embodiments of the present disclosure shows significantly high sterilization power as compared to Comparative Example 1 and Comparative Example 2 of irradiating only blue light and only UV light, respectively throughout the whole duration regardless of an amount of energy. In addition, the light irradiation apparatus according to one or more embodiments of the present disclosure shows the tendency that the sterilization power is increased as an amount of energy is increased.

Experimental Example 4—Sterilization Power Test 4 of First Light and Second Light In the present test, an MRSA strain was used as a pathogen. After the MRSA strain was cultured, a suspension having a constant bacteria concentration (7 log) was prepared. The first light and the second light were irradiated to the bacteria suspension in each light amount. In this case, the wavelength of the first light was 405 nm and the wavelength of the second light was 275 nm. The bacteria irradiated with the first light and the second light were each diluted at a specific concentration, inoculated into agar plates, and then cultured again. Thereafter, the number of colonies of the cultured bacteria was identified, and the numerical value was converted into a log value. Each test was performed under the same conditions five times.

Figure 10A:
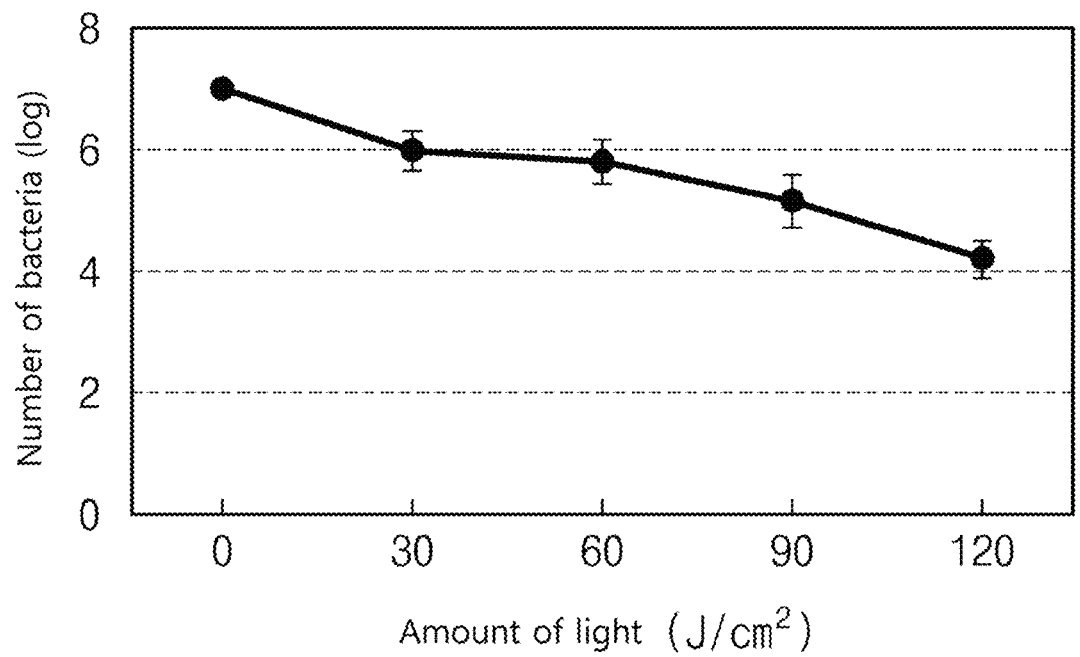
FIG. 10A is a graph illustrating a test result of sterilization power of first light.
Figure 10B:
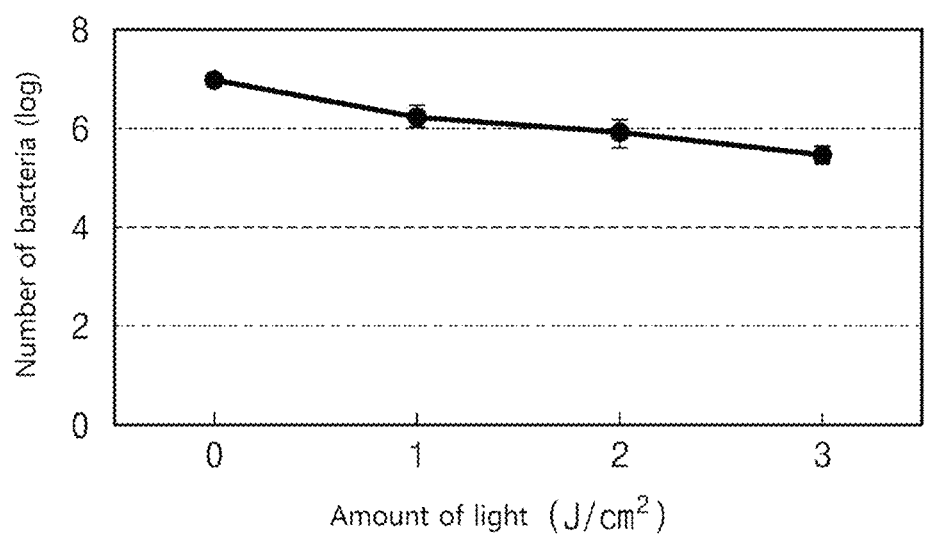
FIG. 10B is a graph illustrating a test result of sterilization power of second light.

Table 4 and FIG. 10A illustrate the test result for the sterilization power of the first light, and Table 5 and FIG. 10B illustrate the test result for the sterilization power of the second light.

TABLE 4

| Light amount (J/cm$^2$) | 0 | 30 | 60 | 90 | 120 |
|---|---|---|---|---|---|
| The number of bacteria | 7.00 | 5.97 | 5.78 | 5.15 | 4.17 |
| Error | 0.00 | 0.32 | 0.35 | 0.43 | 0.29 |

It may be recognized from Table 4 and FIG. 10A that, as an amount of the first light, which is irradiated, is increased, the number of the bacteria is reduced. It is clear that the number of bacteria is reduced even if the margin of error is considered.

TABLE 5

| Light amount (J/cm$^2$) | 0 | 1 | 2 | 3 |
|---|---|---|---|---|
| The number of bacteria | 7.00 | 6.23 | 5.88 | 5.45 |
| Error | 0.00 | 0.23 | 0.27 | 0.18 |

It may be recognized from Table 5 and FIG. 10B that, as an amount of the second light, which is irradiated, is increased, the number of the bacteria is reduced. It is clear that the number of bacteria is reduced even if the margin of error is considered. In addition, it is recognized that the second light sterilizes the bacteria in amount smaller than an amount of the first light.

Experimental Example 5—Sterilization Power Test in Combination of First Light and Second Light In the present test, an MRSA strain was used as a pathogen. After the MRSA strain was cultured, a suspension having a constant bacteria concentration (7 log) was prepared. The individual irradiation of the first light, the individual irradiation of the second light, and the combination of the first light and the second light were performed with respect to the bacteria suspension. Comparative example 1 illustrates that non-light is irradiated to the bacteria suspension, Comparative example 2 illustrates that the second light was individually irradiated to the bacteria suspension, Comparative example 3 illustrates that the first light was individually irradiated to the bacteria suspension, and Embodiment illustrates that the combination of the first light and the second light was irradiated to the bacteria suspension. In this case, the wavelength of the first light was 405 nm, the dose of the first light was 120 J/cm$^2$, and the wavelength of the second light was 275 nm, and the dose of the second light was 3 mJ/cm$^2$. In Embodiment, the second light was irradiated in the dose of 3 mJ/cm$^2$ and then the first light was irradiated in the dose of 120 J/cm$^2$. Next, in Comparative Examples 1 to 3 and Embodiment, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 11A:
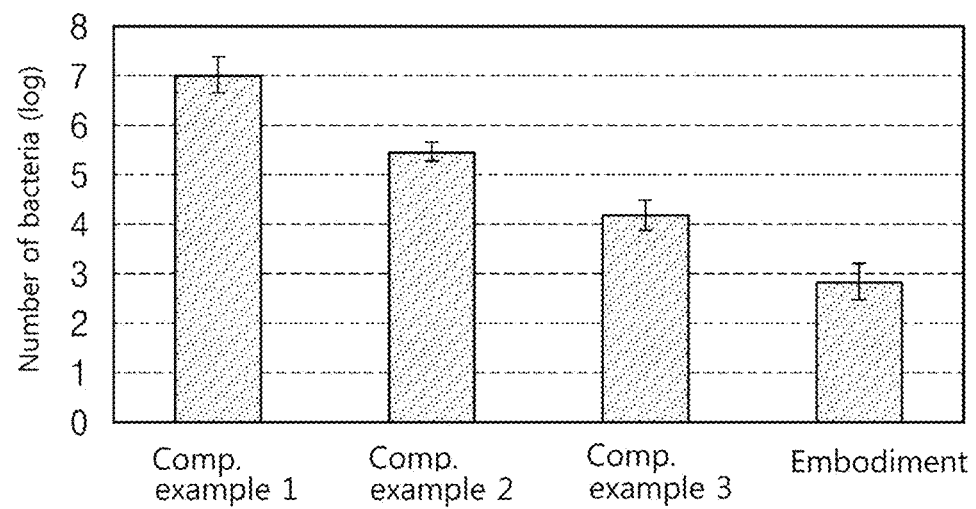
FIG. 11A illustrates the number of bacteria when first light is individually irradiated, when second light is individually irradiated, and when the first light and the second light are combined to be irradiated.
Figure 11B:
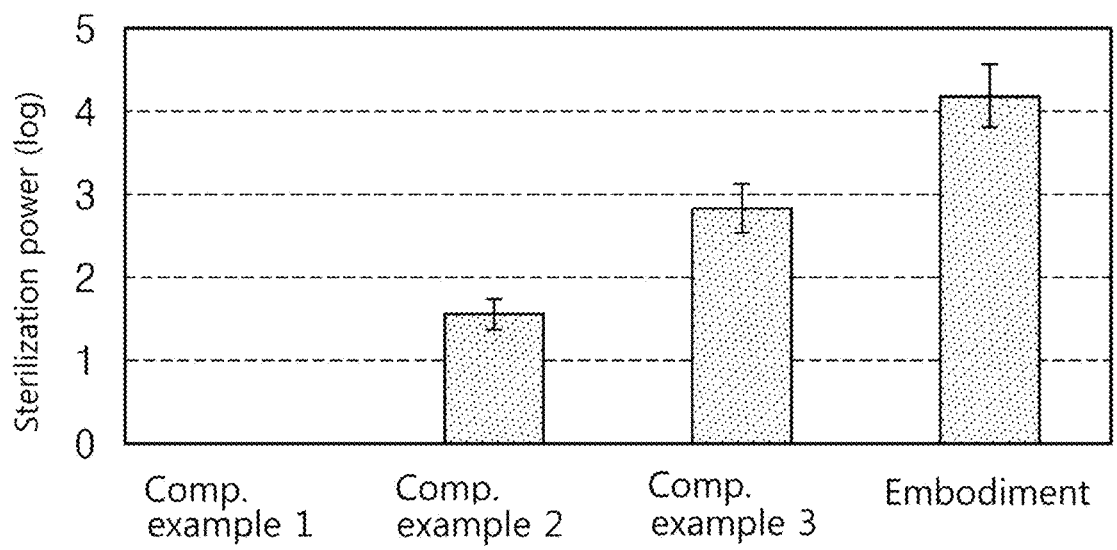
FIG. 11B illustrates sterilization power when first light is individually irradiated, when second light is individually irradiated, and when the first light and the second light are combined to be irradiated.

FIG. 11A and Table 6 illustrate the number of bacteria in the individual irradiation of the first light, the individual irradiation of the second light, and the irradiation of the combination of the first light and the second light. FIG. 11B and Table 7 illustrate the sterilization power in the individual irradiation of the first light, the individual irradiation of the second light, and the irradiation of the combination of the first light and the second light.

TABLE 6

| Light condition | Comparative Example 1 | Comparative Example 2 | Comparative Example 3 | Embodiment |
|---|---|---|---|---|
| The number of bacteria | 7.00 | 5.45 | 4.17 | 2.83 |
| Error | 0.00 | 0.18 | 0.29 | 0.37 |

TABLE 7

| Light condition | Comparative Example 1 | Comparative Example 2 | Comparative Example 3 | Embodiment |
|---|---|---|---|---|
| Sterilization power | 0.00 | 1.55 | 2.83 | 4.17 |
| Error | 0.00 | 0.18 | 0.29 | 0.37 |

Referring to FIGS. 11A, 11B, Table 6, and Table 7, about 90% of sterilization power was illustrated in the individual irradiation of the second light, about 99% of sterilization power was illustrated in the individual irradiation of the first light, and 99.99% or more of sterilization power was illustrated in irradiation of the combination of the first light and the second light. Accordingly, it may be recognized that an amount of bacteria is significantly reduced, and thus the sterilization power is significantly increased when the combination of the first light and the second light is irradiated, as compared to when the light is not irradiated, and to when the first light or the second light is individually irradiated.

Experimental Example 6-Test for Variation in Sterilization Power Based on Sequence of Combining First Light and Second Light In the present test, an MRSA strain was used as a pathogen. After the MRSA strain was cultured, a suspension having a constant bacteria concentration (7 log) was prepared. After the second light was irradiated to the bacteria suspension, the first light was irradiated to the bacteria suspension. In addition, the second light was irradiated to the bacteria suspension after the first light was irradiated to the bacterial suspension. Comparative example 1 illustrates that non-light was irradiated to the bacteria suspension, Embodiment 1 illustrates that the first light was irradiated to the bacteria suspension after the second light was irradiated to the bacteria suspension, and Embodiment 2 illustrates that the second light was irradiated to the bacteria suspension after the first light was irradiated to the bacteria suspension.

In Embodiment 1, after the second light having the wavelength of 275 nm was irradiated to the bacteria suspension with a dose of 3 mJ/cm$^2$, the first light having the wavelength of 405 nm was irradiated to the bacteria suspension with a dose of 120 J/cm$^2$. In Embodiment 2, after the first light having the wavelength of 405 nm was irradiated to the bacteria suspension with a dose of 120 J/cm$^2$, the second light having the wavelength of 275 nm was irradiated with the dose of 3 mJ/cm$^2$.

Next, in Comparative Example, Embodiment 1, and Embodiment 2, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 12A:
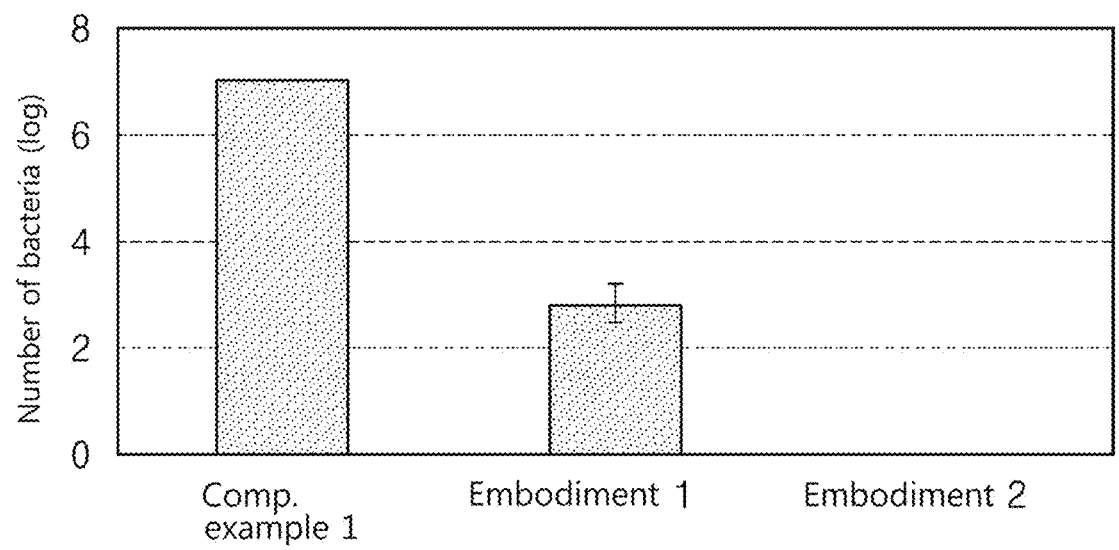
FIG. 12A illustrates the number of bacteria irradiated with light obtained by differently setting the sequence of combining first light and second light.
Figure 12B:
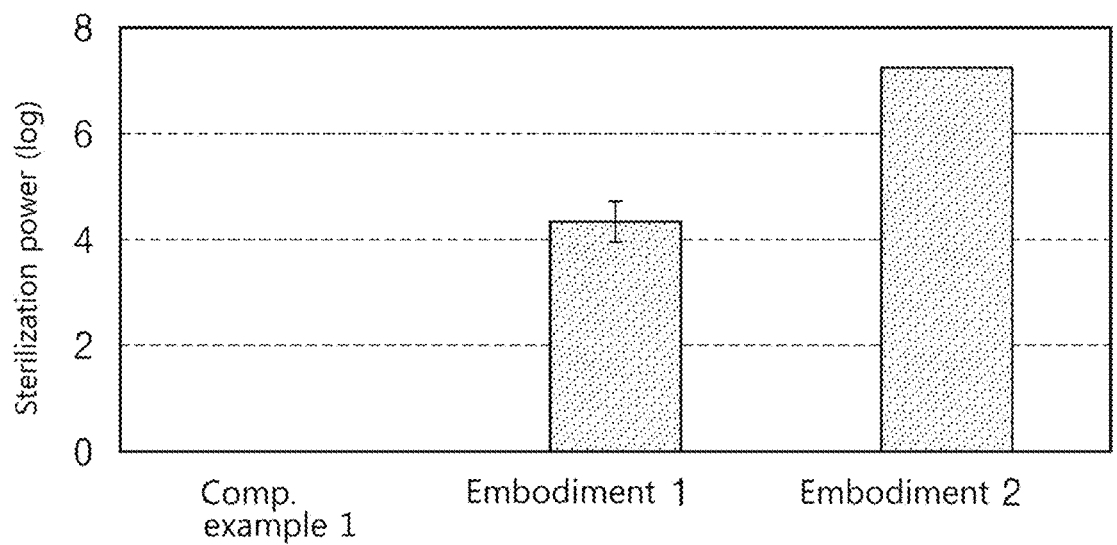
FIG. 12B illustrates sterilization power obtained by differently setting the sequence of combining the first light and the second light.

FIG. 12A and Table 8 illustrate the number of bacteria when the sequence of combining the first light and the second light is differently set, and FIG. 12B and Table 9 illustrate the sterilization power when the sequence of combining the first light and the second light is differently set.

TABLE 8

| Light condition | Comparative Example | Embodiment 1 | Embodiment 2 |
|---|---|---|---|
| The number of bacteria | 7.00 | 2.83 | 0.00 |
| Error | 0.00 | 0.37 | 0.00 |

TABLE 9

| Light condition | Comparative Example | Embodiment 1 | Embodiment 2 |
|---|---|---|---|
| Sterilization power | 0.00 | 4.17 | 7.00 |
| Error | 0.00 | 0.37 | 0.00 |

Referring to FIGS. 12A, 12B, Table 8, and Table 9, Embodiment 1 illustrates 99.99% of sterilization power, and bacteria are not observed in Embodiment 2, so the sterilization is substantially completely achieved.

In other words, the case that the second light is irradiated after the first light is irradiated shows significantly higher sterilization power with the same irradiation amount of light, as compared to the case the first light is irradiated after the second light is irradiated, which means that the same sterilization power is obtained with a smaller amount of light as compared to the case the first light is irradiated after the second light is irradiated. The application of a smaller amount of light means the reduction in the light irradiation time. Accordingly, the light irradiation time is more reduced in Embodiment 2 than in Embodiment 1.

Experimental Example 7—Setting Condition of Amount of Light (In Vitro)

The number of bacteria and the sterilization power were measured as function of an amount of light in vitro condition when the first light and the second light is sequentially irradiated, to find out the optimal amount of each light, based on that the sequential irradiation of the first light and the second light shows the increase in the sterilization power.

In the present test, an MRSA strain was used as a pathogen. After the MRSA strain was cultured, a suspension having a constant bacteria concentration (7 log) was prepared. The first light and the second light were sequentially irradiated to the bacteria suspension by changing the dose of the first light to 30 J/cm$^2$, 60 J/cm$^2$, 90 J/cm$^2$, and 120 J/cm$^2$. However, in the case of the second light, the light of 275 nm was employed with a dose limited to 3 mJ/cm$^2$ based on the allowable level of the human body.

Next, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 13A:
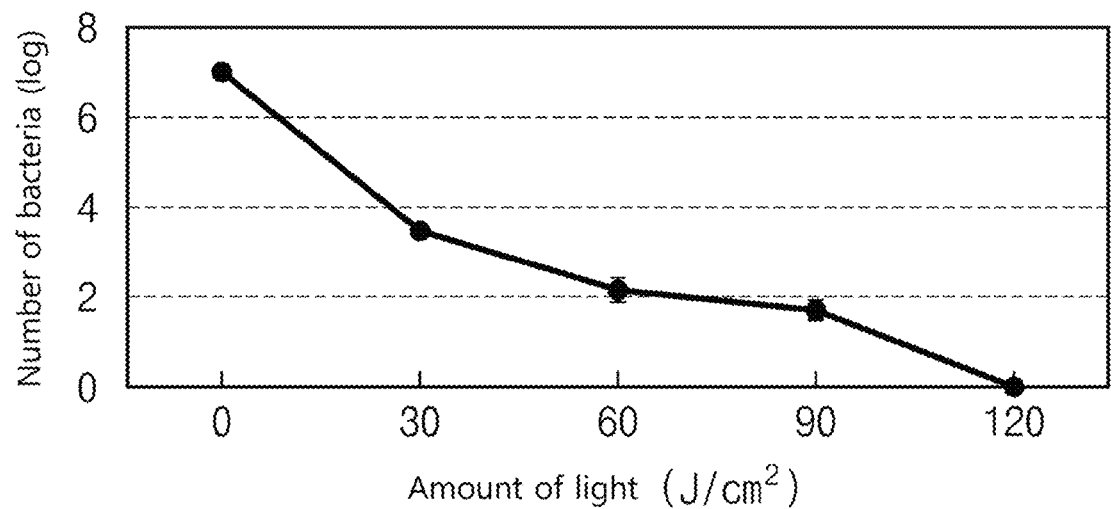
FIG. 13A illustrates the number of bacteria as a function of an amount of the first light in vitro condition when first light and second light were sequentially irradiated.
Figure 13B:
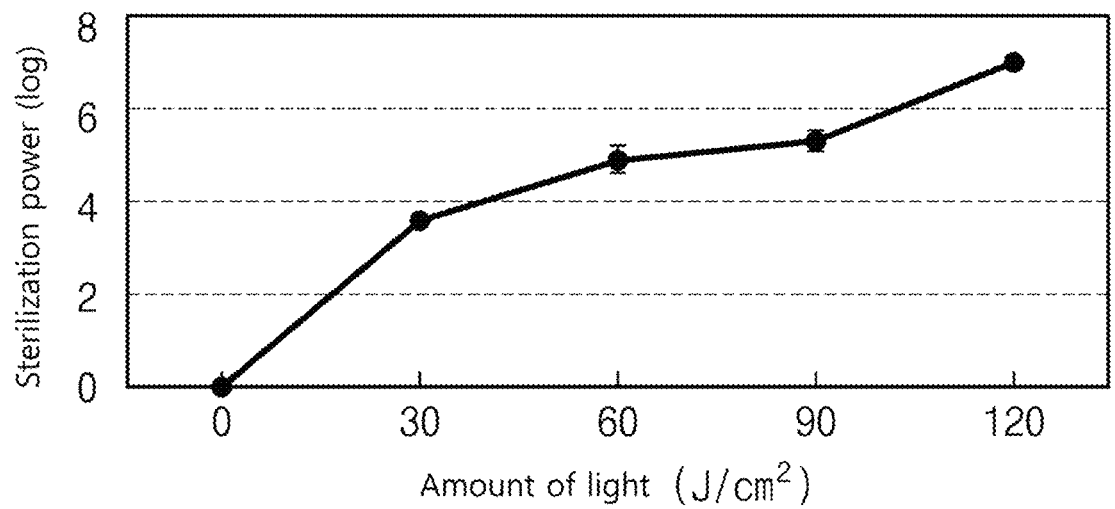
FIG. 13B illustrates sterilization power as a function of the amount of the first light in vitro condition when the first light and the second light were sequentially.

FIG. 13A and Table 10 show the number of bacteria when an amount of the first light is variously set while the first light and the second light are sequentially irradiated, and FIG. 13B and table 11 show the sterilization power when an amount of the first light is variously set while the first light and the second light are sequentially irradiated.

TABLE 10

| Light amount (J/cm$^2$) | 0 | 30 | 60 | 90 | 120 |
|---|---|---|---|---|---|
| The number of bacteria | 7.00 | 3.47 | 2.13 | 1.70 | 0.00 |
| Error | 0.00 | 0.13 | 0.27 | 0.22 | 0.00 |

TABLE 11

| Light amount (J/cm$^2$) | 0 | 30 | 60 | 90 | 120 |
|---|---|---|---|---|---|
| Sterilization power | 0.00 | 3.53 | 4.87 | 5.03 | 7.00 |
| Error | 0.00 | 0.13 | 0.27 | 0.22 | 0.00 |

It may be recognized from FIGS. 13A, 13B, Table 10, and Table 11 that the number of bacteria is reduced as an amount of the first light is increased and the sterilized is completely achieved with a dose of 120 J/cm$^2$.

Experimental Example 8—Setting of Light Amount Condition (In Vivo)

It was recognized through Experiment Example 7 that the sterilization is completely achieved when a dose of the first light (having the wavelength of 275 nm) is 120 J/cm$^2$, under the condition that the dose of the second light (having the wavelength of 405 nm) is 3 mJ/cm$^2$. Accordingly, the test was performed to determine whether the above sterilization effect is obtained under in vivo condition.

The present test was performed using a mouse to determine whether the application of light is effective and safe under in vivo condition. The condition for an amount of light is set to the same condition as that in vitro. For the mouse, a BALB/c mouse (6-8 weeks old) was used, the back of the mouse was shaved, and then a cut was formed in the diameter of 10 mm in the back of the mouse. After the pathogenic bacteria was inoculated (at 5 log) on the wound, the first light and the second light were sequentially irradiated by changing the dose of the first light to 30 J/cm$^2$, 60 J/cm2, 90 J/cm2, and 120 J/cm2. However, in the case of the second light, the light of 275 nm was employed with a dose limited to 3 mJ/cm$^2$ based on the allowable level of the human body. Next, tissues were sampled, and the sampled tissues were disrupted, diluted at a specific concentration, inoculated on agar plates, and then cultured again. Thereafter, the number of colonies of the cultured bacteria was identified, and the numerical value was converted into a log value.

Each test was performed under the same conditions five times.

Figure 14A:
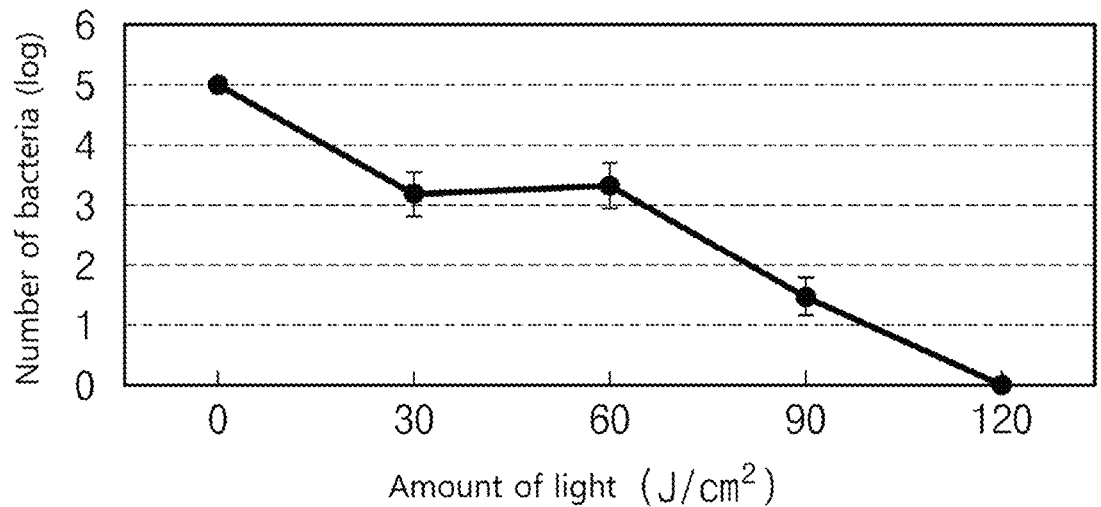
FIG. 14A illustrates the number of bacteria as a function of an amount of the first light in vivo condition, when first light and second light were sequentially irradiated.
Figure 14B:
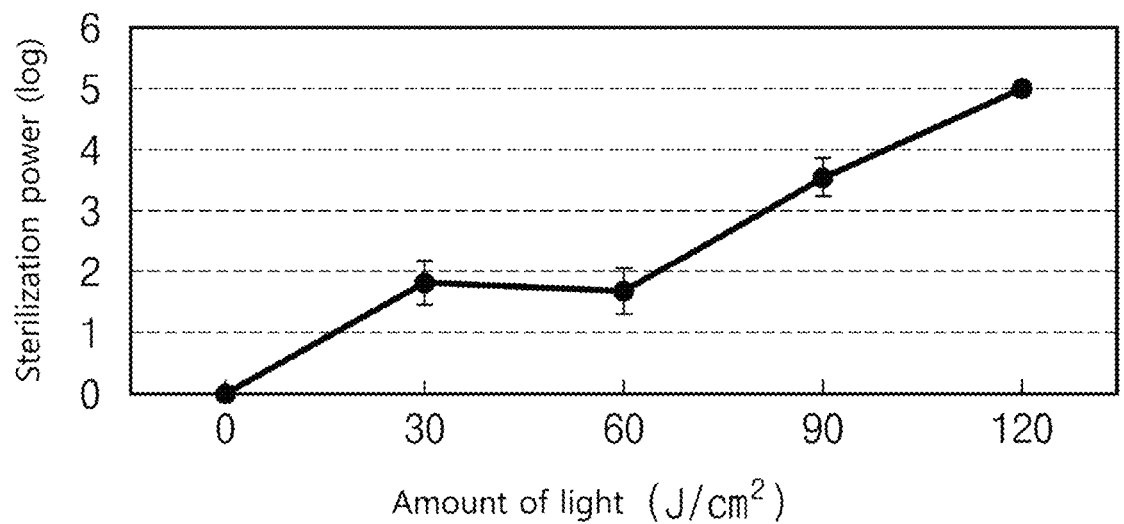
FIG. 14B illustrates the sterilization power as a function of an amount of the first light in vivo condition, when the first light and the second light were sequentially irradiated.

FIG. 14A and Table 12 show the number of bacteria as a function of an amount of the first light, when the first light and the second light were sequentially irradiated. FIG. 14B and Table 13 show the sterilization power as a function of an amount of the first light, when the first light and the second light were sequentially irradiated.

TABLE 12

| Light amount (J/cm$^2$) | 0 | 30 | 60 | 90 | 120 |
|---|---|---|---|---|---|
| The number of bacteria | 5.00 | 3.17 | 3.32 | 1.48 | 0.00 |
| Error | 0.00 | 0.36 | 0.38 | 0.31 | 0.00 |

TABLE 13

| Light amount (J/cm$^2$) | 0 | 30 | 60 | 90 | 120 |
|---|---|---|---|---|---|
| Sterilization power | 0.00 | 1.83 | 1.68 | 3.52 | 5.00 |
| Error | 0.00 | 0.36 | 0.38 | 0.31 | 0.00 |

It may be recognized from FIGS. 14A, 14B, Table 12, and Table 13 that the number of bacteria is reduced as an amount of the first light is increased under in vivo condition and the sterilized is completely achieved with a dose of 120 J/cm$^2$.

Experimental Example 9—Effectiveness Evaluation 1 (In Vivo)

In Experimental Example 8, a dose of light for sterilization was recognized under in vivo condition, and the variation in the sterilization power and the variation in the number of bacteria as functions of time were tested under in vivo condition.

The present test was performed using a mouse. For the mouse, a BALB/c mouse (6-8 weeks old) was used, the back of the mouse was shaved, and then a cut was formed in the diameter of 10 mm in the back of the mouse. After the pathogenic bacteria was inoculated (at 5 log) on the wound, the first light and the second light were sequentially irradiated and repeatedly irradiated six times in total at the same time every day while a dose of the first light (having the wavelength of 405 nm) is 120 J/cm$^2$. In the case of the second light, the light of 275 nm was employed with a dose limited to 3 mJ/cm$^2$ based on the allowable level of the human body.

Next, to determine the number of bacteria every day, tissues were sampled, and the sampled tissues were disrupted, diluted at a specific concentration, inoculated on agar plates, and then cultured again. Thereafter, the number of colonies of the cultured bacteria was identified, and the numerical value was converted into a log value. To determine the initial sterilization power, the number of bacteria was detected until three-time light irradiation.

Figure 15:
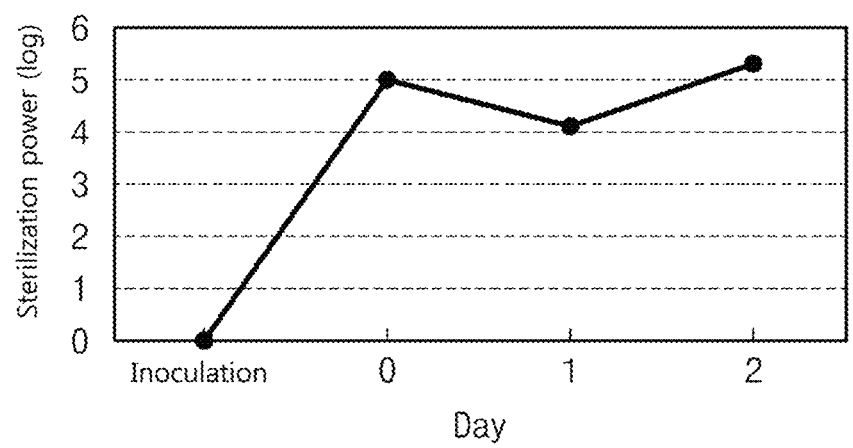
FIG. 15 is a graph illustrating the variation in sterilization power based on days in vivo condition.
Figure 16:
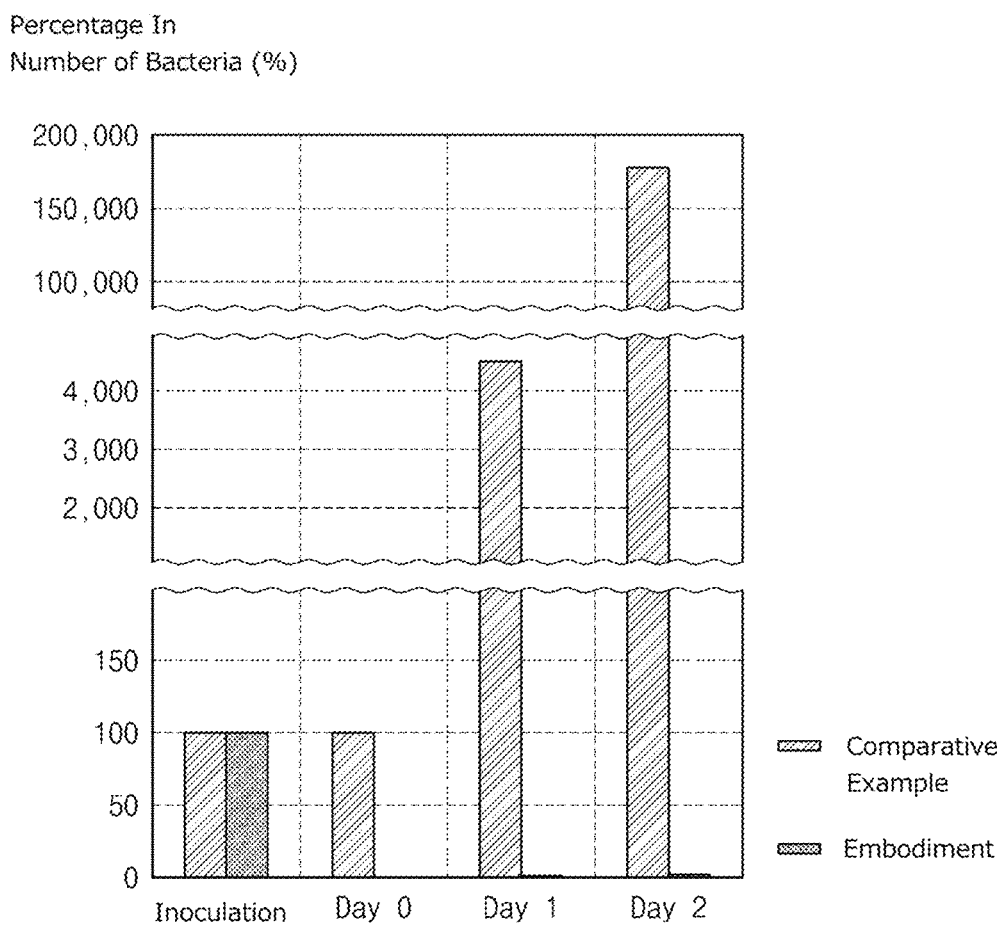
FIG. 16 is a graph illustrating the measurement result of the number of the bacteria based on days in vivo condition.

FIG. 15 and Table 14 show the variation in the sterilization power depending on days under in vivo condition, and FIG. 16 and Table 15 show the measurement result of the number of bacteria in each day under in vivo condition. In FIG. 16 and Table 15, Comparative example is a non-irradiation group without light irradiation, and Embodiment corresponds to a light irradiation group irradiated with light.

TABLE 14

| Day | Inoculation | 0 | 1 | 2 |
|---|---|---|---|---|
| Sterilization power | 0.00 | 5.00 | 4.09 | 5.29 |
| Error | 0.00 | 0.00 | 0.13 | 0.09 |

TABLE 15

| Day | The number of bacteria (%) | | | | The number of bacteria (log) | | | |
|---|---|---|---|---|---|---|---|---|
| | Inoculation | 0 | 1 | 2 | Inoculation | 0 | 1 | 2 |
| Non-irradiation group | 100 | 100 | 4,466 | 173,780 | 5.00 | 5.00 | 6.65 | 8.24 |
| Light irradiation group | 100 | 0 | 0.36 | 0.89 | 5.00 | 0.00 | 2.56 | 2.95 |

Referring to FIG. 15, FIG. 16, Table 14, and Table 15, the sterilization power is continuously maintained to 99.99% or more after light is irradiated to the wound at the initial stage, and the number of bacteria is substantially approximate to '0' when the light is irradiated.

Experimental Example 10—Effectiveness Evaluation 2 (In Vivo)

In Experimental Example 8, a dose of light for sterilization was recognized under in vivo condition, and the effect of curing the wound by irradiating the light was tested under in vivo condition based on the dose of light for sterilization.

The present test was performed using a mouse. For the mouse, a BALB/c mouse (6-8 weeks old) was used, the back of the mouse was shaved, and then a wound was formed in the diameter of 10 mm in the back of the mouse. After the pathogenic bacteria was inoculated (at 5 log) on the wound, the first light and the second light were sequentially irradiated and repeatedly irradiated six times in total at the same time every day while a dose of the first light (having the wavelength of 405 nm) is 120 J/cm$^2$. However, in the case of the second light, the light of 275 nm was employed with a dose limited to 3 mJ/cm$^2$ based on the allowable level of the human body.

The variation in the shape (especially, an area) of the wound was observed at the same time every day. The size of the wound was observed every day till epithelialization, and the value thereof was recorded.

Figure 17:
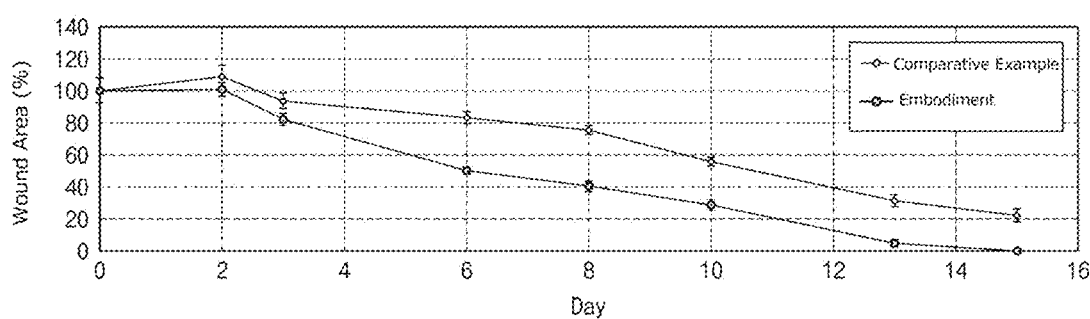
FIG. 17 is a graph illustrating the variation in an area of a wound based on days in vivo condition.
Figure 18A:
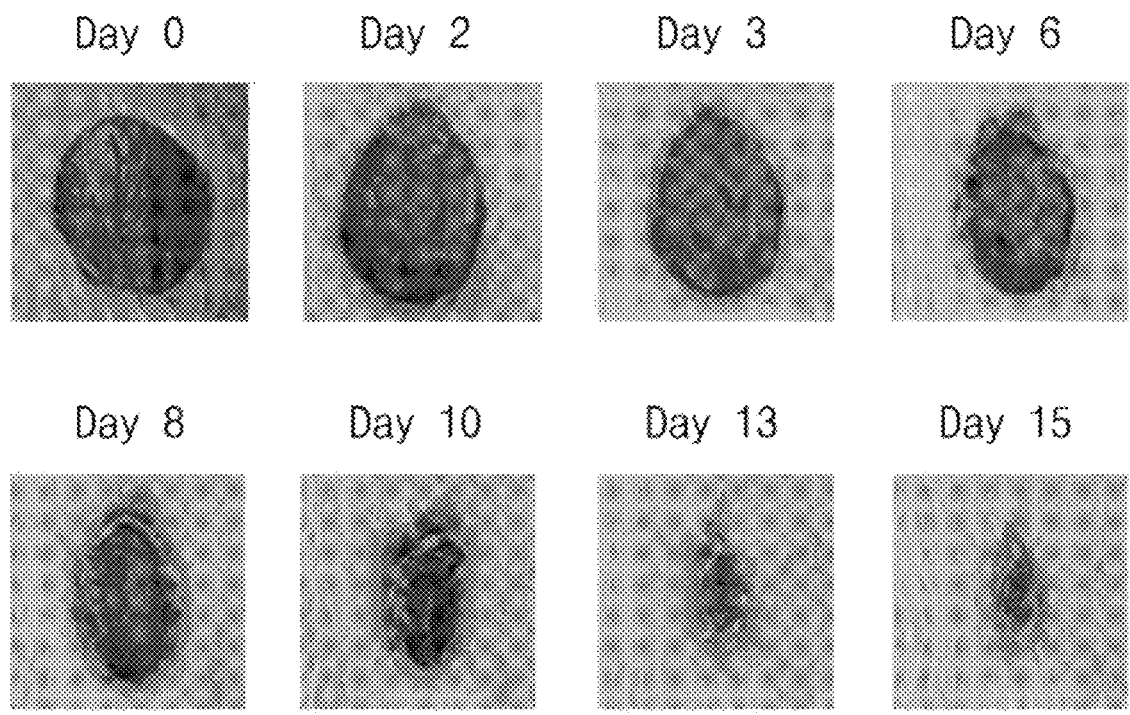
Figure 18B:
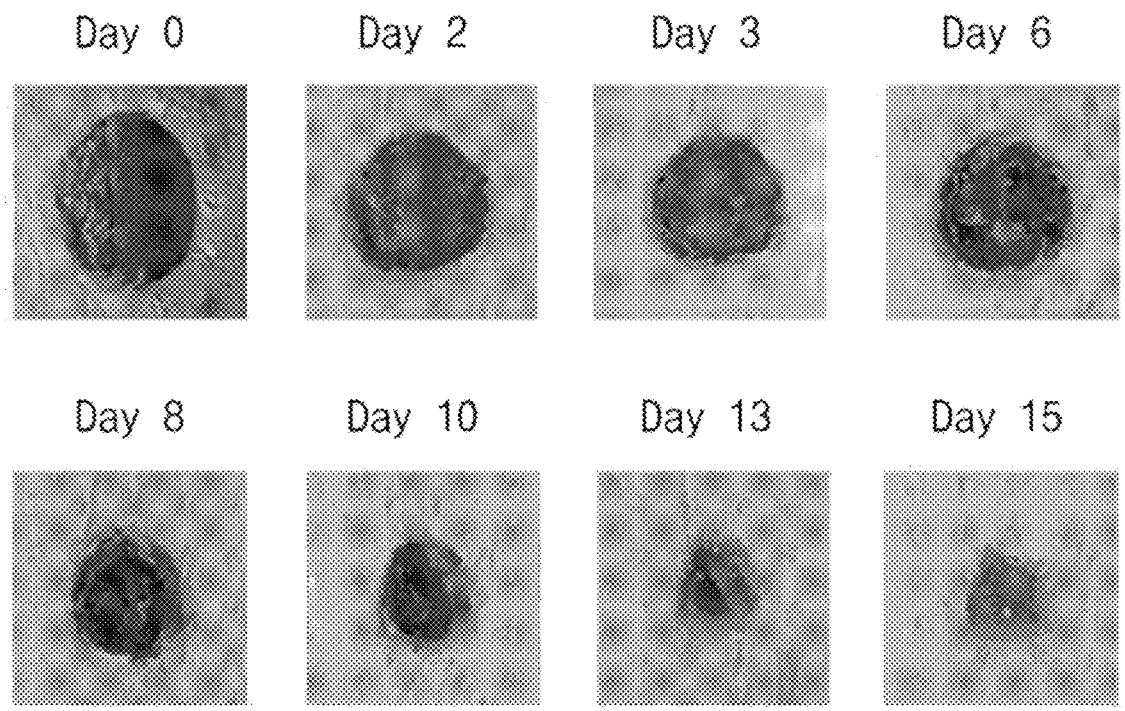

FIG. 17 and Table 16 show the variation in the area of a wound depending on days under in vivo condition. In FIG. 17 and Table 16, Comparative example is a non-irradiation group without light irradiation, and Embodiment corresponds to a light irradiation group irradiated with light. FIGS. 18A and 18B are photographs obtained by capturing images of the shape of the wound area depending on days. FIG. 18A illustrates photographs of a wound in the non-irradiation group, and FIG. 18B illustrates photographs of wounds in the light irradiation group.

TABLE 16

| | Day | | | | | | |
|---|---|---|---|---|---|---|---|
| | Inoculation | 0 | 2 | 3 | 6 | 10 | 15 |
| Non-irradiation group | 100.0 | 100.0 | 108.8 | 93.8 | 83.3 | 55.9 | 22.4 |
| Error | 7.8 | 7.8 | 7.0 | 5.0 | 3.8 | 2.7 | 4.2 |
| Light irradiation group | 100.0 | 100.0 | 101.0 | 82.1 | 50.3 | 28.8 | 0.0 |
| Error | 7.8 | 7.8 | 4.1 | 3.6 | 1.9 | 3.2 | 0.0 |

Referring to FIG. 17, Table 18, FIG. 18A, and FIG. 18B, the wound cured was not visibly observed until 2 days from the wound, and the number of bacteria in the wound was significantly reduced. Accordingly, it was determined that the sterilization was in progress. A scab was produced from 2 days after the wound and then the area of the wound was gradually reduced. Accordingly, the curing of the wound is in progress from 2 days after the wound. When the scab was produced on the wound, the wound exposed to the outside was disappeared by the scab. Therefore, the additional infection is less caused. However, the size of the scab and the recovery rate of the wound were greatly varied depending on the sterilization state until the scab was formed. Although the light irradiation group required 6 days till a time point at which the area of the wound was reduced to 50% in the stage of curing the wound, the non-irradiation group required 10 days till the time point. Further, the epithelialization was achieved on the $1_5$th day in the case of the light irradiation group, and not achieved in the case of the non-irradiation group. Accordingly, according to one or more embodiments of the present disclosure, it may be recognized that the significant effect of curing the wound appears when light is irradiated.

Experimental Example 11—Safety Evaluation 1 (In Vivo)

In the above-described experimental example, a DNA mutation state was determined to determine whether the irradiation condition is harmful to the human body.

In the present test, to determine whether the DNA mutation was caused to the tissue which is not infected through light irradiation, the formation degree of a thymine dimer was determined through immunohistochemical analysis. When an excessive amount of UV is irradiated to the DNA, the DNA mutation such as the thymine dimer is caused, so the cell is destroyed. Accordingly, the DNA mutation may be determined based on the formation degree of the thymine dimer.

The present test was performed using a mouse. For the mouse, a BALB/c mouse (6-8 weeks old) was used, the back of the mouse was shaved, and then a wound is formed in the diameter of 10 mm in the back of the mouse by using the punch. After light was irradiated on the wound, the tissue was sampled, the sampled tissue was fixed through formalin and paraffin, and a cut-out fragment was taken. When light was irradiated, the control group was a non-irradiation group in which light was not treated, Experimental group 1 was a light irradiation group in which an excessive amount of UVC was treated, Experimental group 2 was a light irradiation group in which the first light and the second light were sequentially irradiated in the state that a dose of the first light (having the wavelength of 405 nm) is limited to 120 J/cm$^2$ and, a dose of the second light (having the wavelength of 275 nm) is limited to 3 mJ/cm$^2$.

Figure 19A:
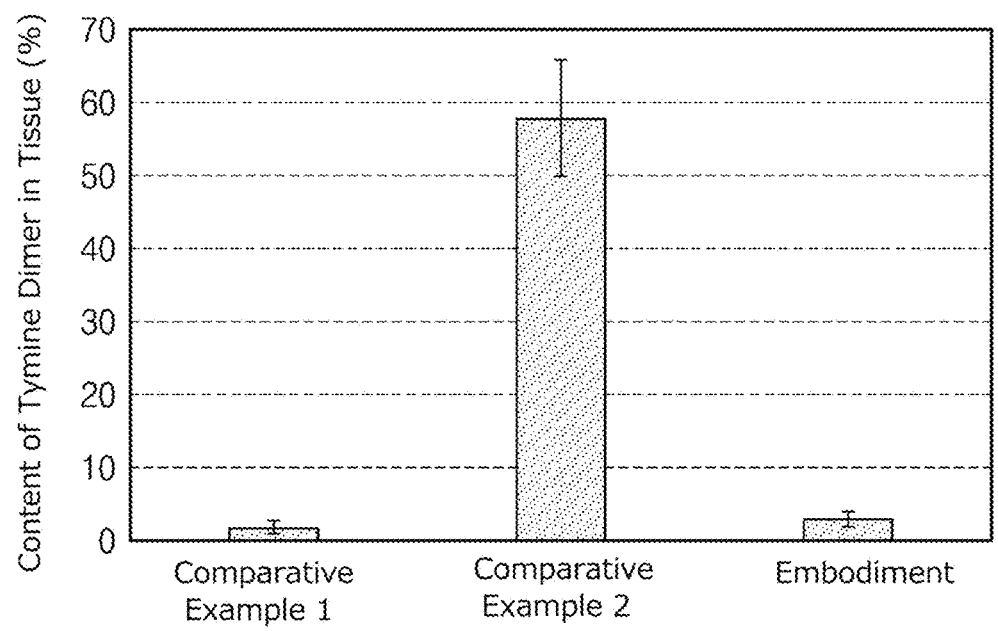
FIG. 19A is a graph illustrating the percentage of a thymine dimer in a tissue.

FIG. 19A and Table 17 illustrate the percentage of a thymine dimer in a tissue. Referring to FIG. 19A and Table 17, although the thymine dimer was found in Experimental group 1, the thymine dimer was not found in Experimental group 2. Accordingly, under the light condition applied according to one or more embodiments of the present disclosure, it was determined that the DNA mutation was not found even if the light was irradiated to a tissue which was not infected.

TABLE 17

|  | Control group | Experimental group 1 | Experimental group 2 |
|---|---|---|---|
| Content (%) | 2 | 58 | 3 |
| Error | 1 | 8 | 1 |

Experimental Example 12—Safety Evaluation 1 (In Vivo)

In the above-described experimental example, the generation state of ROS was determined to determine whether the irradiation condition was harmful to the human body.

The present test is to determine whether the ROS was induced even in the tissue, which was not infected, through light irradiation. When the sterilizing light was irradiated to the infectious bacteria, the ROS was induced to destroy the bacteria.

The present test was performed using a mouse. For the mouse, a BALB/c mouse (6-8 weeks old) was used, the back of the mouse was shaved, and then a wound is formed in the diameter of 10 mm in the back of the mouse by using the punch. After the light was irradiated on the wound, a Dichlorofluorescin diacetate (DCFH-DA) was treated for a part irradiated with light and a light emission was measured with respect to a part stained with DCFH-DA, so it was determined that the ROS was present. DCFH-DA was oxidized by the ROS in the cell to emit fluorescent light. When DCFH-DA was excited, the absorption wavelength was in the range of 445 nm to 490 nm, and the fluorescent wavelength was in the range of 515 nm to 575 nm.

In this case, the control group was a non-treatment group in which non-treatment is added, Experimental group 1 was a group treated with hydrogen peroxide, and Experimental group 2 was a treatment group to which the first light and the second light are sequentially irradiated in the state that a dose of the first light (having the wavelength of 405 nm) is limited to 120 J/cm², and a dose of the second light (having the wavelength of 275 nm) is limited to 3 mJ/cm².

Figure 19B:
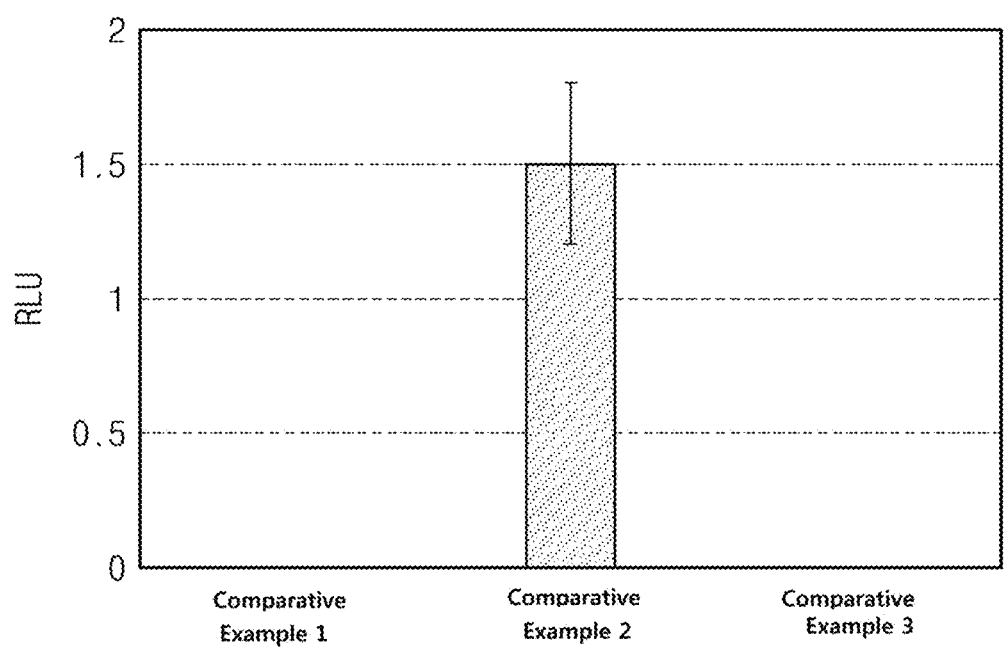
FIG. 19B illustrates a light emission degree of a part stained with DCFH-DA.

FIG. 19B and Table 18 illustrate the light emission degree of a part stained with DCFH-DA. Referring to FIG. 19B and Table 18, fluorescent is emitted in Experimental group 1, so it is determined that ROS is present. However, since fluorescent is not absent in Experiment group 2, so it is determined that ROS is absent in Experiment group 2. Accordingly, under the light condition applied according to one or more embodiments of the present disclosure, it was determined that the ROS was not produced even if the light was irradiated to a tissue which was not infected.

TABLE 18

|  | Control group | Experimental group 1 | Experimental group 2 |
|---|---|---|---|
| Light emission degree (RLU; relative light units) | 0 | 1.5 | 0 |
| Error | 0 | 0.3 | 0 |

Experimental Example 13—Sterilization Power Test in Supplying Oxygen

In the present experiment, sterilization power was tested depending on whether oxygen is additionally supplied when the first light is irradiated. In the present experimental example, the used strain was *Staphylococcus aureus*, a bacteria suspension was irradiated with the first light of a 405 nm wavelength and the contact count with air (that is, the contact with oxygen) was increased by using the stirrer. The initial concentration of the bacteria suspension was 1×10⁶ CFU/mL, and the first light source was disposed at a predetermined height from a plate having the bacteria suspension and irradiated the first light. The suspension irradiated with the first light was diluted to a specific concentration, inoculated into agar plates, and then cultured again. Thereafter, the number of colonies of the cultured bacteria was identified, and the numerical value thereof was converted into a log value, thereby measuring the sterilization power.

Figure 20:
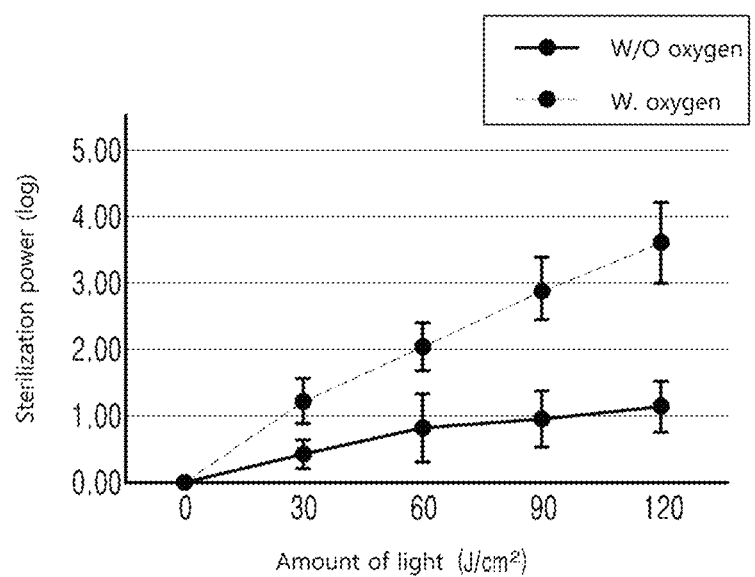
FIG. 20 illustrates sterilization power measured based on an amount of the first light depending on oxygen is present.

FIG. 20 and Table 19 show the sterilization power based on an amount of the first light and the P-value thereof which were measured.

TABLE 19

|  |  | Amount of light (J/cm²) | | | | |
|---|---|---|---|---|---|---|
|  |  | 0 | 30 | 60 | 90 | 120 |
| Without Oxygen | Sterilization Power | 0.00 | 0.44 | 0.86 | 0.98 | 1.15 |
|  | Error | 0.00 | 0.22 | 0.48 | 0.42 | 0.40 |
| With Oxygen | Sterilization Power | 0.00 | 1.24 | 2.06 | 2.94 | 3.64 |
|  | Error | 0.00 | 0.34 | 0.36 | 0.47 | 0.62 |
|  | P-value | — | 0.0225 | 0.0304 | 0.0083 | 0.0055 |

Referring to FIG. 20 and Table 19, it can be understood that the sterilization power is significantly increased, when oxygen is continuously supplied by increasing the contact time with the air and the contact count with the air by using the stirrer.

As described above, the sterilizing device according to one or more embodiments of the present disclosure shows sterilization power more excellent than a sterilizing device using only a specific wavelength.

The sterilizing device according to one or more embodiments of the present disclosure may be applied to various other devices requiring sterilization, and particularly, may be applied to a device using a light source. For example, the sterilizing device according to one or more embodiments of the present disclosure may be applied to medical facilities, such as operating rooms and hospitals or a light irradiation apparatus for public hygiene or personal hygiene. In particular, the light irradiation apparatus according to one or more embodiments of the present disclosure may be used for the purpose of treating a patient or for surgical and hospital purposes such as sterilization of an operating part during the surgical procedure. In addition, the light irradiation apparatus is applied to a human body to be used for infection treatment and infection prevention in acute or chronic wounds. In addition, the sterilizing device may be used for the treatment and the prevention of the infection caused by bacteria having resistance against conventional antibiotics.

The light irradiation apparatus according to the present disclosure is applied to public facilities, a public space, and common use products to be used to improve public hygiene, or is applied to personal facilities, a personal space, and personal use products to be used to improve personal hygiene.

In addition, the sterilizing device according to the present disclosure may be used for a lighting device as the sterilizing device is added to the lighting device as well as performing the intrinsic function thereof.

Figure 21:
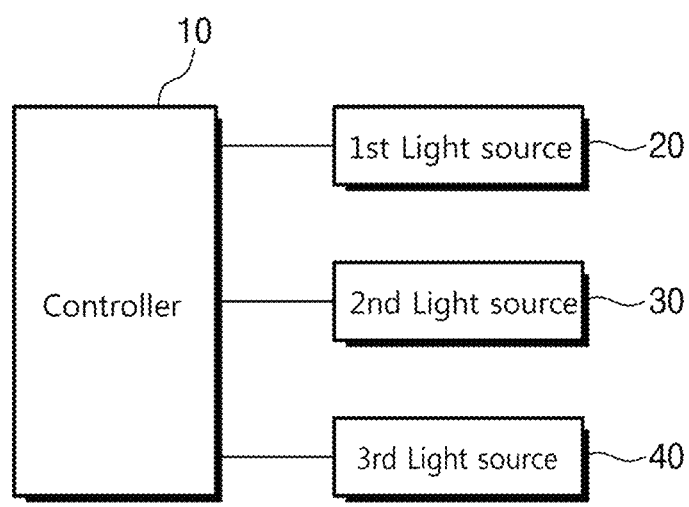
FIG. 21 is a block diagram illustrating that a light irradiation apparatus is used as a lighting device, according to one or more embodiments of the present disclosure.

FIG. 21 is a view illustrating that the light irradiation apparatus according to one or more embodiments of the present disclosure is used for a lighting device. FIG. 21 is a block diagram illustrating that the light irradiation apparatus further includes an additional light source in addition to the first light source 20 and the second light source 30.

Referring to FIG. 21, the light irradiation apparatus according to one or more embodiments of the present disclosure may further include a third light source 40 to provide light to a specific space. The third light source 40 may emit light having a third wavelength in the visible light band. The third light may emit light corresponding to the whole spectrum of the visible light band and may emit light corresponding to a spectrum of a specific color.

In the present embodiment, the light irradiation apparatus is used for the lighting device by turning on or turning off the third light source 40, while sterilizing a specific space by driving the first light source 20 and the second light source 30. In this case, the third light source 40 is connected with the controller 10 such that the operation of the third light source 40 is controlled by the controller 10.

In one or more embodiments of the present disclosure, the first to third light sources 20, 30, and 40 may be driven independently of each other. For example, time may be set to individually turn on/off the first to third light sources 20, 30, and 40. However, in this case, the duration that the first and second light sources 20 and 30 are simultaneously operated is necessarily provided. Alternatively, although the first and second light sources 20 and 30 are driven together to be simultaneously turned on/off, the third light source 40 may be independently driven separately from the first and second light sources 20 and 30. For example, in the state that the third light source 40 is turned on, the first and second light sources 20 and 30 are turned on/off only for a specific time or several times at regular time intervals. In one or more embodiments of the present disclosure, the first and second light sources 20 and 30 may be periodically turned on at regular time intervals in a public place where continuous sterilization management is required The sterilizing device according to one or more embodiments of the present disclosure may further include additional components that perform other functions, in addition to the above-described components.

Figure 22:
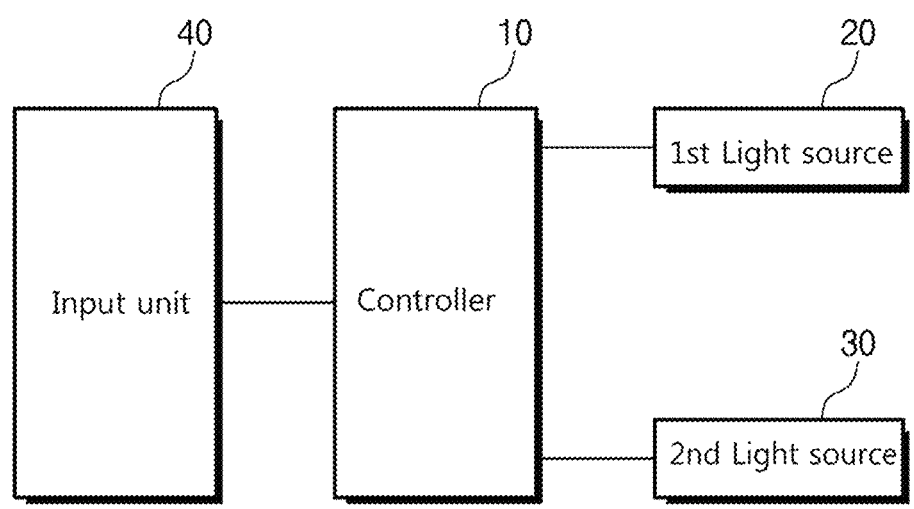
FIG. 22 is a block diagram illustrating a light irradiation apparatus, according to one or more embodiments of the present disclosure.

FIG. 22 is a block diagram illustrating light irradiation apparatus, according to one or more embodiments of the present disclosure;

Referring to FIG. 22, the light irradiation apparatus may receive various data and be driven in response to input data. To this end, the light irradiation apparatus according to one or more embodiments of the present disclosure may further include an input unit 50 to input data.

The input unit 50 is to input data, such as data of a user, data of a target to be sterilized, or data of a surrounding, which exerts an influence on an irradiation amount of light from the first and second light sources 20 and 30, the irradiation intensity of the light, and the irradiation time of the light. For example, the input unit 50 is to input the type of a microorganism to be sterilized or the extent contaminated by the microorganism. The controller 10 controls an irradiation amount of light from the first and second light sources 20 and 30, the irradiation intensity of the light, and the irradiation time of the light, based on the data.

In an embodiment of the inventive step, the input unit 50 may be provided in various forms such as a keyboard, a touch screen, or a button, but the type of the input unit 50 is not limited thereto.

Although an exemplary embodiment of the inventive concept has been described for illustrative purposes, those skilled in the art will appreciate that various modifications, and substitutions are possible, without departing from the scope and spirit of the invention as disclosed in the accompanying claims.

Accordingly, the technical scope of the inventive concept is not limited to the detailed description of this specification, but should be defined by the claims.

We claim:

1. A light irradiation apparatus, comprising:
a first light source including a first n type semiconductor layer, a first active layer disposed on the first n type semiconductor layer, and a first p type semiconductor layer disposed on the first active layer;
a second light source including a second n type semiconductor layer, a second active layer disposed on the second n type semiconductor layer, and a second p type semiconductor layer disposed on the second active layer, wherein the first and second light sources emit first light and second light, respectively, at timings close to each other, regardless of whether the timings overlap or not, the first light being emitted based on a first band gap difference of a first energy band resulting from an intrinsic material of the first active layer and the second light being emitted based on a second band gap difference of a second energy band resulting from an intrinsic material of the second active layer;
a controller in communication with the first light source and the second light source and configured to control the first light source and the second light source,
wherein the controller is further configured to allow to (1) start an application of the first light to a target to be sterilized starts at a predetermined time before a first application of the second light to the target, and (2) apply the first light to the target without interruption until the application of the first light is finished, and
wherein the controller is further configured to allow a second application of the second light to the target to occur after the application of the first light is finished; and
wherein a dose of the second light source is less than 1/10 of a dose of the first light source.

2. The light irradiation apparatus of claim 1, wherein a wavelength of the first light is in a range of about 400 nm to about 420 nm, or a range of about 455 nm to about 470 nm.

3. The light irradiation apparatus of claim 1, wherein the second light corresponds to a wavelength of ultraviolet C (UVC).

4. The light irradiation apparatus of claim 3, wherein the wavelength of the second light is in a range of about 210 nm to about 280 nm.

5. The light irradiation apparatus of claim 3, wherein the wavelength of the second light is in a range of about 220 nm to about 230 nm.

6. The light irradiation apparatus of claim 1, wherein the first light and the second light are simultaneously emitted during the first application of the second light.

7. The light irradiation apparatus of claim 1, wherein a duration of the first application of the second light is at least partially overlapped with a duration in which the first light is emitted.

8. The light irradiation apparatus of claim 7, wherein the second light is emitted in an on and off manner.

9. The light irradiation apparatus of claim 1, wherein a duration of the second application of the second light is not overlapped with a duration in which the first light is emitted.

10. The light irradiation apparatus of claim 1, wherein an irradiation area of the first light source is overlapped with an irradiation area of the second light source.

11. The light irradiation apparatus of claim 1, wherein the controller controls at least one of an intensity and an irradiation duration of each of the first light and the second light.

12. The light irradiation apparatus of claim 11, further comprising:
a third light source connected with the controller to emit light having a visible light wavelength.

13. The light irradiation apparatus of claim 12, further comprising:
an oxygenator connected with the controller and supplying oxygen.

14. The light irradiation apparatus of claim 12, further comprising:
an input unit connected with the controller to input data on a user or an external environment,
wherein the controller controls the first and second light sources based on the data from the input unit.

15. The light irradiation apparatus of claim 1, wherein the second light applied to a human body is in a range of about 30 $J/m^2$ to about 1,000,000 $J/m^2$.

16. The light irradiation apparatus of claim 1, wherein the light irradiation apparatus is configured to operate as a medical device for treating a human body.

17. The light irradiation apparatus of claim 1, wherein the light irradiation apparatus is configured to operate as a medical device for curing an acute wound.

18. A light irradiation apparatus, comprising:
a first light source including a first n type semiconductor layer, a first active layer disposed on the first n type semiconductor layer, and a first p type semiconductor layer disposed on the first active layer, the first light source configured to emit first light;
a second light source including a second n type semiconductor layer, a second active layer disposed on the second n type semiconductor layer, and a second p type semiconductor layer disposed on the second active layer, the second light source configured to emit second light;
a controller in communication with the first light source and the second light source and configured to control the first light source and the second light source,
wherein the controller is further configured to allow to (1) start an application of the first light to a target to be sterilized at a predetermined time before a first application of the second light to the target and (2) apply the first light is applied to the target without interruption until the application of the first light is finished, and
wherein the controller is further configured to allow a second application of the second light to the target to occur after the application of the first light is finished; and
wherein the first and second light sources emit the first light and the second light, respectively, at timings close to each other, regardless of whether the timings overlap or not, the first light being emitted based on a first band gap difference of a first energy band resulting from an intrinsic material of the first active layer and the second light being emitted based on a second band gap difference of a second energy band resulting from an intrinsic material of the second active layer.

19. The light irradiation apparatus of claim 18, wherein the active layer further includes an additional first layer and an additional second layer.

* * * * *